(12) United States Patent
Wolff et al.

(10) Patent No.: US 7,473,419 B2
(45) Date of Patent: *Jan. 6, 2009

(54) INTRAVASCULAR DELIVERY OF NUCLEIC ACID

(75) Inventors: Jon A. Wolff, Madison, WI (US); James E. Hagstrom, Middleton, WI (US); Hans Herweijer, Madison, WI (US); Vladimir G. Budker, Middleton, WI (US); Julia Hegge, Monona, WI (US)

(73) Assignee: Roche Madison Inc., Madison, WI (US)

( * ) Notice: Subject to any disclaimer, the term of this patent is extended or adjusted under 35 U.S.C. 154(b) by 368 days.

This patent is subject to a terminal disclaimer.

(21) Appl. No.: 11/268,276

(22) Filed: Nov. 7, 2005

(65) Prior Publication Data

US 2006/0093584 A1 May 4, 2006

Related U.S. Application Data

(60) Division of application No. 11/008,856, filed on Dec. 10, 2004, now Pat. No. 7,015,040, and a continuation-in-part of application No. 10/855,175, filed on May 27, 2004, which is a continuation-in-part of application No. 10/085,378, filed on Feb. 27, 2002, now Pat. No. 6,897,068, and a continuation-in-part of application No. 09/707,000, filed on Nov. 6, 2000, said application No. 10/085,378 and a continuation-in-part of application No. 09/450,315, filed on Nov. 29, 1999, now Pat. No. 6,379,966.

(60) Provisional application No. 60/121,730, filed on Feb. 26, 1999, provisional application No. 60/146,564, filed on Jul. 30, 1999, provisional application No. 60/163,719, filed on Nov. 5, 1999, provisional application No. 60/473,654, filed on May 28, 2003, provisional application No. 60/500,211, filed on Sep. 4, 2003.

(51) Int. Cl.
*A01N 63/00* (2006.01)
*A61K 48/00* (2006.01)

(52) U.S. Cl. ............... 424/93.2; 435/455; 435/456; 514/44

(58) Field of Classification Search ............... None
See application file for complete search history.

(56) References Cited

U.S. PATENT DOCUMENTS 7,214,369 B2 * 5/2007 Wolff et al. ............ 424/93.2

* cited by examiner

*Primary Examiner*—James S Ketter
(74) *Attorney, Agent, or Firm*—Kirk Ekena; Mark K. Johnson

(57) ABSTRACT

Disclosed is a process for providing for expression of an exogenous nucleic acid in an extravascular parenchymal cell of a mammal. The nucleic acid is inserted into a vessel of a mammal and the permeability of the vessel is increased. Increasing permeability of the vessel allows delivery of the nucleic acid to an extravascular parenchymal cell.

36 Claims, 15 Drawing Sheets

A.

B.

A.

B.

A.

B.

A.

B.

INTRAVASCULAR DELIVERY OF NUCLEIC ACID

CROSS-REFERENCE TO RELATES APPLICATIONS

This application is a divisional of application Ser. No. 11/008,856, filed Dec. 10, 2004, now U.S. Pat No. 7,015,040 which is a continuation-in-part of application Ser. No. 10/085,378, filed Feb. 27, 2002, now U.S. Pat. No. 6,897,068 application Ser. No. 09/707,000, filed Nov. 6, 2000, application Ser. No. 10/855,175, filed May 27, 2004, application Ser. No. 10/085,378 is a continuation-in-part of application Ser. No. 09/450,315, filed Nov. 29, 1999, issued as U.S. Pat. No. 6,379,966, which claims the benefit of U.S. Provisional Applications No. 60/121,730, filed Feb. 26, 1999, and 60/146,564, filed Jul. 30, 1999, application Ser. No. 09/707,000 claims the benefit of U.S. Provisional Application No. 60/163,719, filed Nov. 5, 1999, and application Ser. No. 10/855,175 claims the benefit of U.S. Provisional Applications No. 60/473,654 filed on May 28, 2003 and 60/500,211 filed Sept. 4, 2003.

FIELD OF THE INVENTION

The invention relates to compounds and methods for use in biologic systems. More particularly, processes that transfer nucleic acids into cells are provided. Nucleic acids in the form of naked DNA or a nucleic acid combined with another compound are delivered to cells.

BACKGROUND OF THE INVENTION

Gene therapy is the purposeful delivery of genetic material to cells for the purpose of treating disease or biomedical investigation and research. Gene therapy includes the delivery of a polynucleotide to a cell to express an exogenous nucleotide sequence, to inhibit, eliminate, augment, or alter expression of an endogenous nucleotide sequence, or to produce a specific physiological characteristic not naturally associated with the cell. In some cases, the polynucleotide itself, when delivered to a cell, can alter expression of a gene in the cell. A basic challenge in gene therapy is to develop approaches for delivering genetic information to cells in vivo in a way that is efficient and safe. If genetic material are appropriately delivered they can potentially enhance a patient's health and, in some instances, lead to a cure. Delivery of genetic material to cells in vivo is also beneficial in basic research into gene function as well as for drug development and target validation for traditional small molecule drugs. Therefore, a primary focus of gene therapy is based on strategies for delivering genetic material in the form of nucleic acids.

Delivery of a nucleic acid means to transfer a nucleic acid from a container outside a mammal to near or within the outer cell membrane of a cell in the mammal. The term transfection is used herein, in general, as a substitute for the term delivery, or, more specifically, the transfer of a nucleic acid from directly outside a cell membrane to within the cell membrane. The transferred (or transfected) nucleic acid may contain an expression cassette. If the nucleic acid is a primary RNA transcript that is processed into messenger RNA, a ribosome translates the messenger RNA to produce a protein within the cytoplasm. If the nucleic acid is a DNA, it enters the nucleus where it is transcribed into a messenger RNA that is transported into the cytoplasm where it is translated into a protein. Therefore if a nucleic acid expresses its cognate protein, then it must have entered a cell. A protein may subsequently be degraded into peptides, which may be presented to the immune system.

It was first observed that the in vivo injection of plasmid DNA into muscle enabled the expression of foreign genes in the muscle (Wolff J A et al. 1990). Since that report, several other studies have reported the ability for foreign gene expression following the direct injection of DNA into the parenchyma of other tissues. Naked DNA was expressed following its injection into cardiac muscle (Acsadi G et al. 1991). While intra-arterial delivery of polynucleotides to limb skeletal muscle cells has proven to be effective, the procedure is not readily clinically viable.

SUMMARY OF THE INVENTION

In a preferred embodiment, a process is described for delivering a polynucleotide into an extravascular parenchymal cell of a mammal, comprising selecting a polynucleotide to be delivered, inserting the polynucleotide into a mammalian vessel, such as a blood vessel and increasing the permeability of the vessel such that the polynucleotide is delivered to the parenchymal cell thereby altering endogenous properties of the cell. Increasing the permeability of the vessel comprises increasing pressure against vessel walls. Increasing the pressure consists of injecting an appropriate volume of fluid into the vessel at an appropriate rate. The volume of fluid comprises the polynucleotide in a pharmaceutically acceptable solution into the vessel. The fluid may further comprise a compound which complexes with the polynucleotide. The fluid may further comprise a compound known to cause vessel dilation. The increased pressure is controlled by altering the specific volume of the solution in relation to the specific time period of insertion. Increasing the permeability of a vessel may further comprise inhibiting the flow of fluid through one or more vessels. Increasing the permeability of a vessel may further comprise inhibiting fluid flow or into or out of an organ or limb.

In one embodiment, a process described for delivering a polynucleotide to a cell in a mammalian limb comprising, impeding blood flow into and/or out of the limb and inserting the polynucleotide in a solution into the lumen of a vein in the limb at a site distal to the occlusion. The polynucleotide is delivered to limb cells distal to the occlusion. The vein may be occluded before, during and after the injection. In a preferred embodiment, the cell is an extravascular cell in a mammalian limb.

In a preferred embodiment, the process further comprises administration of at least one anesthetic or analgesic drug or adjuvant. Administration of anesthetics or analgesic lessens potential discomfort or pain experienced by the mammal during or after the procedure. Examples of such drugs lidocaine, NSAIDs, clonidine, ketamine, neuromuscular blockers, and immunsuppressants.

In a preferred embodiment, a complex for providing nucleic acid delivery to cell and expression in the cell is provided, comprising: a polynucleotide/polymer complex wherein the zeta potential of the complex is not positive. The complex can be delivered to an in vivo cell using the described process.

In another embodiment, a process is described for delivering a polynucleotide-containing non-viral complex into a parenchymal cell of a mammal, comprising: making the polynucleotide-compound complex wherein the compound is selected from the group consisting of amphipathic compounds, polymers and non-viral vectors, inserting the polynucleotide into a mammalian vessel and increasing the permeability of the vessel thereby delivering the polynucleotide to the parenchymal cell.

In a preferred embodiment, inhibiting the flow of fluid comprises: impeding fluid flow through veins or arteries of the target tissue by applying external compression against mammalian skin. This compression includes applying a cuff over the skin, such as a sphygmomanometer (or other device with a bladder that is inflated) or a tourniquet. Fluid flow through a vessel may also be impeded by clamping the vessel or by a balloon catheter placed within the vessel. The vessels are occluded for a period of time necessary to deliver the polynucleotide without causing ischemic damage to the tissue. The solution is injected into the limb vein distal to the occlusion. The solution is injected using an injection device selected from the group comprising: catheter, syringe needle, cannula, stylet, balloon catheter, multiple balloon catheter, single lumen catheter, and multilumen catheter.

In one embodiment, the polynucleotide may be selected from the group comprising: naked polynucleotide, viral particle, viral vector, non-viral vector polynucleotide-containing non-viral complex, expression cassette, and functional polynucleotide that is not expressed but has activity in a cell.

The described method can be used to deliver a polynucleotide to a mammalian cell for the purpose of altering the endogenous properties of the cell, for example altering the endogenous properties of the cell for therapeutic purposes, for augmenting function, for facilitating pharmaceutical drug discovery, for facilitating drug target validation or for investigating gene function (i.e., research).

In one embodiment, the extravascular parenchymal cell consists of a limb (leg or arm) muscle cell selected from the group consisting of: skeletal muscle cells (myofiber, myocytes) bone cells (osteocytes, osteoclasts, osteoblasts), bone marrow cells, stroma cells, joint cells (synovial and cartilage cells), connective tissue cells (fibroblasts, fibrocytes, chondrocytes, mesenchyme cells, mast cells, macrophages, histiocytes), cells in tendons cells in the skin and cells in the lymph nodes. In another embodiment, the parenchymal cells is selected from the group comprising: cardiac muscle cell, liver cell, hepatocyte, kidney cell, spleen cell, pancreatic cell, prostate cell and diaphragm cell.

U.S. application Ser. Nos. 10/085,378, 09/707,000 and 10/855,175 are incorporated herein by reference. Further objects, features, and advantages of the invention will be apparent from the following detailed description when taken in conjunction with the accompanying drawings.

FIG. 15A-15F. Photomicrographs from three different lower limb muscle groups stained for β-galactosidase following a single intravenous injection of 40 mg of pDNA (pCI-LacZ) into a distal site of the great saphenous vein. (A-B) gastrocnemius muscle, (C-D) soleus muscle, (E-F) extensor hallucis brevis. Individual panels indicate representative high-expressing areas in two different locations of each muscle group.

Figure 16:
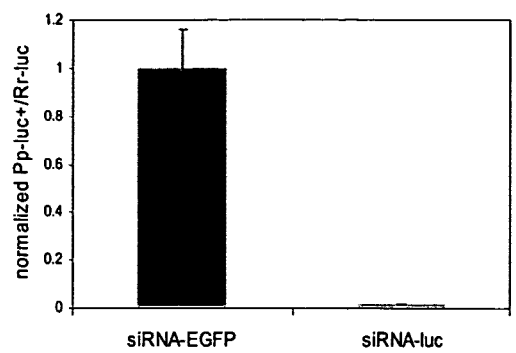
Figure 16:
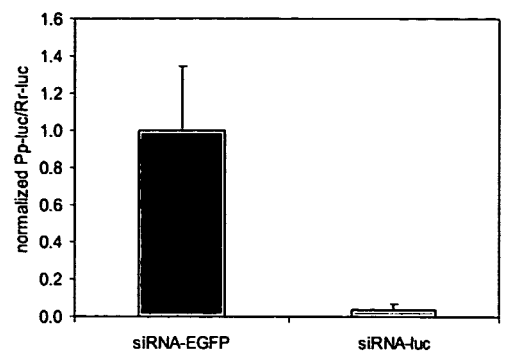

FIG. 16. RNA interference in rat and primate limb muscle following intravenous co-delivery of siRNAs and pDNA expression vectors. Firefly luciferase knockdown in limb muscle using the targeted siRNA was plotted against firefly luciferase knockdown using the control siRNA (EGFP) that was normalized to 1. (16A) rat, (516B) monkey.

DETAILED DESCRIPTION

We have found that an intravascular route of administration allows a polynucleotide to be delivered to a parenchymal cell in a more even distribution than direct parenchymal injections. The efficiency of polynucleotide delivery and expression is increased by increasing the permeability of the tissue's blood vessel. Permeability is increased by one or more of the following: increasing the intravascular pressure, delivering the injection fluid rapidly (injecting the injection fluid rapidly), using a large injection volume, inhibiting vessel fluid flow, and injecting a compound known to increase permeability of the vessel wall. Using the describe process, polynucleotides can be delivered to a large number of mammalian organs including, but not limited to: liver, spleen, lung, kidney, heart, prostate and skeletal muscle. If the polynucleotide contains an expressible sequence, the polynucleotide is expressed therein.

Because of the presence of numerous valves in limb veins, it was believed that intravenous injection was not a viable option for delivering polynucleotides to limb muscle in vivo. Injection towards increased branching of the vein, as is done in arterial injection, would be blocked by these valves and would potentially damage the valves. However, the described invention provides processes to the use of the venous system to deliver polynucleotides to cells outside of the vascular system whereby the polynucleotides are injected into a vein in the limb in an anterograde direction (in the direction of normal blood flow; FIG. 1). Intravenous delivery of polynucleotides provides a number of advantages. The venous system is a direct conduit to multiple muscle groups of a limb and provides a direct conduit to the post-capillary venules, which are more permeable to macromolecules than other parts of the microvasculature in muscle (Palade et al. 1978). Vessels of the venous system also have reduced vessel wall thickness relative to comparable arterial vessels and they can be made more permeable than the arterial system thus allowing increased delivery to extravascular locations. Furthermore, some veins are located nearer the surface than arteries and are therefore easily accessed. The venous system is readily accessible to both initial (single) and repeat deliveries. In addition, venous injection combined with the use of a cuff for impeding blood flow provides a non-surgical method for polynucleotide delivery. For certain clinical indications, where the arterial system displays vascular pathology (arteriosclerosis, atherosclerosis, and single or multiple partial or total occlusions), the venous system represents a more attractive delivery conduit to deliver the polynucleotide to the extravascular region of interest, including skeletal muscle cells.

The described delivery system comprises an intravascular administration route. Vessels comprise internal hollow tubular structures connected to a tissue or organ within the body of an animal, including a mammal. Bodily fluid flows to or from the body part within the lumen of the tubular structure. Examples of bodily fluid include blood, lymphatic fluid, or bile. Vessels comprise: arteries, arterioles, capillaries, venules, sinusoids, veins, lymphatics, and bile ducts. Afferent vessels are directed towards the organ or tissue and in which fluid flows towards the organ or tissue under normal physiological conditions. Conversely, efferent vessels are directed away from the organ or tissue and in which fluid flows away from the organ or tissue under normal physiological conditions. A vascular network consists of the directly connecting vessels supplying and/or draining fluid in a target organ or tissue.

A needle, cannula, catheter or other injection device may be used to inject the polynucleotide into the vessel. Single and multi-port injectors may be used, as well as single or multi-balloon catheters and single and multilumen injection devices. A catheter can be inserted at a distant site and threaded through the lumen of a vessel so that it resides in or near a target tissue. The injection can also be performed using a needle that traverses the skin and enters the lumen of a vessel. Occlusion of vessels, by balloon catheters, clamps, or cuffs can limit or define target area. The described intravenous processes require that blood flow be impeded for substantially less time than is required to cause tissue damage by ischemia.

For delivery to a limb, one method for occluding fluid flow is the application of an external cuff. A cuff means an externally applied device for impeding fluid flow to and from a mammalian limb. The cuff applies compression around the limb such that vessels, in an area underneath the cuff, are forced to occlude in an amount sufficient to impede fluid from flowing through the vessels at a normal rate. One example of a cuff is a sphygmomanometer, which is normally used to measure blood pressure. Another example is a tourniquet. A third example is a modified sphygmomanometer cuff containing two air bladders such as is used for intravenous regional anesthesia (i.e. Bier Block). Double tourniquet, double cuff tourniquet, oscillotonometer, oscillometer, and haemotonometer are also examples of cuffs. A sphygmomanometer can be inflated to a pressure above the systolic blood pressure, above 500 mm Hg or above 700 mm Hg or greater than the intravascular pressure generated by the injection.

The polynucleotide is injected in a pharmaceutically acceptable solution. Pharmaceutically acceptable refers to those properties and/or substances which are acceptable to the mammal from a pharmacological/toxicological point of view. The phrase pharmaceutically acceptable refers to molecular entities, compositions and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals, and more particularly in humans.

Polynucleotide delivery is increased by increasing the permeability of a blood vessel within the target tissue. Permeability is defined here as the propensity for macromolecules such as polynucleotides to move through vessel walls and enter the extravascular space. One measure of permeability is the rate at which macromolecules move through the vessel wall and out of the vessel. Another measure of permeability is the lack of force that resists the movement of polynucleotides being delivered to leave the intravascular space. Vessel permeability and extravascular fluid volume is increased by one or more of the following: using a sufficient volume of an appropriate injection solution, injecting the solution at an appropriate rate, impeding fluid flow into and out of the target tissue during the process, and increasing permeability of the vessel wall.

To obstruct, in this specification, is to block or inhibit inflow or outflow of blood in a vessel. Rapid injection may be combined with obstructing the outflow to increase permeability. For example, an afferent vessel supplying an organ is rapidly injected and the efferent vessel draining the tissue is ligated transiently. The efferent vessel (also called the venous outflow or tract) draining outflow from the tissue is also partially or totally clamped for a period of time sufficient to allow delivery of a polynucleotide. In the reverse, an efferent is injected and an afferent vessel is occluded.

The described method is shown to be effective for delivering polynucleotides to limb muscle cells in mouse, rat, rabbit, dog, and nonhuman primate. By increasing the amount of polynucleotide injected and the volume of injection, the method described for delivery of polynucleotides to parenchymal cells in small mammals such as mice or rats is readily adapted to use in larger animals. Injection rate may also be increased for delivery to larger mammals. Conversely, for delivery to smaller animals, the injection volume and/or rate is reduced. For example, efficient delivery to mouse liver may require injection of as little as 1 ml or less (animal weight ~25 g). In comparison, injection volume for rats can be from 6 to 35 ml or greater and efficient delivery to dog or nonhuman primate limb muscle may require as much as 60-500 ml or more (animal weight 3-14 kg).

The injection volume can also be related to the target tissue. For example, delivery of a polynucleotide to a limb can be aided by injecting a volume greater than 5 ml per rat limb or greater than 70 ml for a primate (rhesus monkey). The injection volumes in terms of ml/limb muscle are usually within the range of 0.6 to 1.8 ml/g of muscle but can be greater. In another example, delivery of a polynucleotide to liver in mice can be aided by injecting the polynucleotide in an injection volume about 0.4-1 ml per 10 g animal wt. In another preferred embodiment, delivering a polynucleotide to a limb of a primate (rhesus monkey), the complex can be in an injection volume from 0.6 to 1.8 m/g of limb muscle or anywhere within this range. Occlusion of vessels, by balloon catheters, clamps, cuffs, natural occlusion, etc, can limit or define the vascular network size or target area.

As further examples, for intravenous delivery, for delivery to rat hind limb (150 g animal total weight), injection of 0.2-3 ml injection solution at a rate of 0.5-25 ml/min into the saphenous vein results in delivery of polynucleotides to multiple muscle cells throughout the limb. For IV delivery to beagle dog (~9.5 kg total weight) forelimb, injection of 36-40 ml injection solution at a rate of 2 ml/sec into a limb vein results in delivery of polynucleotides to multiple muscle cells throughout the limb. For delivery to rhesus monkey limb, injection of 40-100 ml injection solution at a rate of 1.7-2 ml/sec into a limb vein results in delivery of polynucleotides to multiple muscle cells throughout the limb. This volume corresponds to from about 0.2 to about 0.6 ml of injection solution per ml of displaced target limb volume in rhesus monkey. Target limb volume is the volume of the limb or portion of the limb distal to the vessel occlusion or isolated by the vessel occlusion. The intravascular injection method results in highly efficient gene delivery to parenchymal cells throughout the target area following a single injection.

One method of determining target size is through volume displacement measurement (for limb target area) or through MRI scan. The precise volume and rate of injection into a particular vessel, for delivery to a particular target tissue of a given mammal species, may also be determined empirically. Because vasculature may not be identical from one individual to another, methods may be employed to predict or control appropriate injection volume and rate. Injection of iodinated contrast dye detected by fluoroscopy can aid in determining vascular bed size. MRI can also be used to determine bed size. Also, an automatic injection system can be used such that the injection solution is delivered at a preset pressure or rate. For such a system, pressure may be measured in the injection apparatus, in the vessel into which the solution is injected, in a branch vessel within the target tissue, or within a vein or artery within the target tissue.

The rate of the injection is partially dependent on the volume to be injected, the size of the vessel to be injected into, and the size of the animal. In one embodiment the total injection volume (for example, 1-3 mls for delivery to mouse liver) can be injected in 4-15 seconds into the vascular system of mice. In another embodiment the total injection volume (6-35 mls) can be injected into the vascular system of rats in about 7-20 seconds. In another embodiment the total injection volume (80-200 mls) can be injected into the vascular system of rhesus monkeys in about 120 seconds or less. Injection rates can vary from 0.5 ml/sec or lower to 4 ml/sec or higher, depending on animal size, vessel size, etc.

Other agents known in the art may be used to further increase vessel permeability, including drugs or chemicals and hypertonic solutions. Drugs or chemicals can increase the permeability of the vessel by causing a change in function, activity, or shape of cells within the vessel wall; typically interacting with a specific receptor, enzyme or protein of the vascular cell. Agents that increase permeability by changing the extracellular connective material may also be used. Examples of drugs or chemicals that may be used to increase vessel permeability include histamine, vascular permeability factor (VPF, which is also known as vascular endothelial growth factor, VEGF), calcium channel blockers (e.g., verapamil, nicardipine, diltiazem), beta-blockers (e.g., lisinopril), phorbol esters (e.g., PKC), ethylenediamine-tetraacetic acid (EDTA), adenosine, papaverine, atropine, and nifedipine. The permeability enhancing drug or chemical may be present in the polynucleotide-containing injection solution. An efflux enhancer solution, a solution containing a permeability enhancing drug or chemical, may also be injected into the vein prior to injection of the solution containing the polynucleotide. Hypertonic solutions have increased osmolarity compared to the osmolarity of blood thus increasing osmotic pressure and causing cells to shrink. Typically, hypertonic solutions containing salts such as NaCl or sugars or polyols such as mannitol are used. Delivery might also be enhanced by pharmacologic agents that cause vasoconstriction or vasodilation. Agents that block or prevent blood clotting (or digest blood clots) may also be injected into the vessel.

Parenchymal Cells

Parenchymal cells are the distinguishing cells of a gland, organ or tissue contained in and supported by the connective tissue framework. The parenchymal cells typically perform a function that is unique to the particular organ. The term "parenchymal" often excludes cells that are common to many organs and tissues such as fibroblasts and endothelial cells within the blood vessels.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that present at least one side to a hepatic sinusoid and an apposed side to a bile canaliculus. Cells in the liver that are not parenchymal cells include the endothelial cells or fibroblast cells within the blood vessels.

In striated muscle, the parenchymal cells include myoblasts, satellite cells, myotubules, and myofibers. In cardiac muscle, the parenchymal cells include the myocardium (also known as cardiac muscle fibers or cardiac muscle cells) and the cells of the impulse connecting system such as those that constitute the sinoatrial node, atrioventricular node, and atrioventricular bundle.

In a pancreas, the parenchymal cells include cells within the acini such as zymogenic cells, centroacinar cells, basal or basket cells and cells within the islets of Langerhans such as alpha and beta cells.

In spleen, thymus, lymph nodes and bone marrow, the parenchymal cells include reticular cells and blood cells (or precursors to blood cells) such as lymphocytes, monocytes, plasma cells and macrophages.

In the nervous system which includes the central nervous system (the brain and spinal cord) peripheral nerves, and ganglia, the parenchymal cells include neurons, glial cells, microglial cells, oligodendrocytes, Schwann cells, and epithelial cells of the choroid plexus.

In glandular tissues and organs, the parenchymal cells include cells that produce hormones. In the parathyroid glands, the parenchymal cells include the principal cells (chief cells) and oxyphilic cells. In a thyroid gland, the parenchymal cells include follicular epithelial cells and parafollicular cells. In adrenal glands, the parenchymal cells include the epithelial cells within the adrenal cortex and the polyhedral cells within the adrenal medulla.

In a lung, the parenchymal cells include the epithelial cells, mucus cells, goblet cells, and alveolar cells.

In fat tissue, the parenchymal cells include adipose cells or adipocytes.

In skin, the parenchymal cells include the epithelial cells of the epidermis, melanocytes, cells of the sweat glands, and cells of the hair root.

In cartilage, the parenchyma includes chondrocytes. In bone, the parenchyma includes osteoblasts, osteocytes, and osteoclasts.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers that contain equal amounts of anions and cations. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations.

In one embodiment, polycations are mixed with polynucleotides for intravascular delivery to a cell. Polycations are a very convenient linker for attaching specific receptors to DNA and as result, DNA/polycation complexes can potentially be targeted to specific cell types. An endocytic step in the intracellular uptake of DNA/polycation complexes is suggested by results in which functional DNA delivery is increased by incorporating endosome disruptive capability into the polycation are transfection vehicle. Polycations also cause DNA condensation. The volume which one DNA molecule occupies in complex with polycations is drastically lower than the volume of a free DNA molecule. The size of DNA/polymer complex may be important for gene delivery in vivo. In terms of intravenous injection, DNA needs to cross the endothelial barrier and reach the parenchymal cells of interest.

Polymers may incorporate compounds that increase their utility. These groups can be incorporated into monomers prior to polymer formation or attached to the polymer after its formation. The gene transfer enhancing moiety is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced. The gene transfer enhancing moiety can be a protein, peptide, lipid, steroid, sugar, carbohydrate, nucleic acid, cell receptor ligand, or synthetic compound. The gene transfer enhancing moieties enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Compounds that enhance release from intracellular compartments can cause DNA release from intracellular compartments such as endosomes (early and late), lysosomes, phagosomes, vesicle, endoplasmic reticulum, Golgi apparatus, trans Golgi network (TGN), and sarcoplasmic reticulum. Release includes movement out of an intracellular compartment into cytoplasm or into an organelle such as the nucleus. Such compounds include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor moieties are any signal that enhances the association of the gene with a cell. This can be accomplished by either increasing the binding of the polynucleotide or polynucleotide complex to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Cleavable Polymers

A prerequisite for gene expression is that once DNA/polymer complexes have entered a cell the polynucleotide must be able to dissociate from the cationic polymer. This may occur within cytoplasmic vesicles (i.e. endosomes), in the cytoplasm, or the nucleus. We have developed bulk polymers prepared from disulfide bond containing co-monomers and cationic co-monomers to better facilitate this process. These polymers have been shown to condense polynucleotides, and to release the nucleotides after reduction of the disulfide bond. These polymers can be used to effectively complex with DNA and can also protect DNA from DNases during intravascular delivery to the liver and other organs. After internalization into the cells the polymers are reduced to monomers, effectively releasing the DNA, as a result of the stronger reducing conditions (glutathione) found in the cell. Negatively charged polymers can be fashioned in a similar manner, allowing the condensed nucleic acid particle (DNA+ polycation) to be "recharged" with a cleavable anionic polymer resulting in a particle with a net negative charge that after reduction of disulfide bonds will release the polynucleic acid. The reduction potential of the disulfide bond in the reducible co-monomer can be adjusted by chemically altering the disulfide bonds environment. This will allow the construction of particles whose release characteristics can be tailored so that the polynucleic acid is released at the proper point in the delivery process.

Cleavable Cationic Polymers

Cationic cleavable polymers are designed such that the reducibility of disulfide bonds, the charge density of polymer, and the functionalization of the final polymer can all be controlled. The disulfide co-monomer can have reactive ends chosen from, but not limited to the following: the disulfide compounds contain reactive groups that can undergo acylation or alkylation reactions. Such reactive groups include isothiocyanate, isocyanate, acyl azide, N-hydroxysuccinimide esters, succinimide esters, sulfonyl chloride, aldehyde, epoxide, carbonate, imidoester, carboxylate, alkylphosphate, arylhalides (e.g. difluoro-dinitrobenzene) or succinic anhydride.

If functional group A (cationic co-monomer) is an amine then B (disulfide containing co-monomer) can be (but not restricted to) an isothiocyanate, isocyanate, acyl azide, N-hydroxysuccinimide, sulfonyl chloride, aldehyde (including formaldehyde and glutaraldehyde), epoxide, carbonate, imidoester, carboxylate, or alkylphosphate, arylhalides (difluoro-dinitrobenzene) or succinic anhydride. In other terms when function A is an amine then function B can be acylating or alkylating agent.

If functional group A is a sulfhydryl then functional group B can be (but not restricted to) an iodoacetyl derivative, maleimide, vinyl sulfone, aziridine derivative, acryloyl derivative, fluorobenzene derivatives, or disulfide derivative (such as a pyridyl disulfide or 5-thio-2-nitrobenzoic acid (TNB) derivatives).

If functional group A is carboxylate then functional group B can be (but not restricted to) a diazoacetate or an amine, alcohol, or sulfhydryl in which carbonyldiimidazole or carbodiimide is used.

If functional group A is an hydroxyl then functional group B can be (but not restricted to) an epoxide, oxirane, or an carboxyl group in which carbonyldiimidazole or carbodiimide or N,N'-disuccinimidyl carbonate, or N-hydroxysuccinimidyl chloroformate is used.

If functional group A is an aldehyde or ketone then function B can be (but not restricted to) an hydrazine, hydrazide derivative, amine (to form a Schiff Base that may or may not be reduced by reducing agents such as $NaCNBH_3$).

The polymer is formed by simply mixing the cationic, and disulfide-containing co-monomers under appropriate conditions for reaction. The resulting polymer may be purified by dialysis or size-exclusion chromatography.

The reduction potential of the disulfide bond can be controlled in two ways. Either by altering the reduction potential of the disulfide bond in the disulfide-containing co-monomer, or by altering the chemical environment of the disulfide bond in the bulk polymer through choice the of cationic co-monomer.

The reduction potential of the disulfide bond in the co-monomer can be controlled by synthesizing new cross-linking reagents. Dimethyl 3,3'-dithiobispropionimidate (DTBP) is a commercially available disulfide containing crosslinker from Pierce Chemical Co. This disulfide bond is reduced by dithiothreitol (DTT), but is only slowly reduced, if at all by biological reducing agents such as glutathione. More readily reducible crosslinkers have been synthesized by Mirus. These crosslinking reagents are based on aromatic disulfides such as 5,5'-dithiobis(2-nitrobenzoic acid) and 2,2'-dithiosalicylic acid. The aromatic rings activate the disulfide bond towards reduction through delocalization of the transient negative charge on the sulfur atom during reduction. The nitro groups further activate the compound to reduction through electron withdrawal which also stabilizes the resulting negative charge.

Cleavable Disulfide Containing Co-Monomers

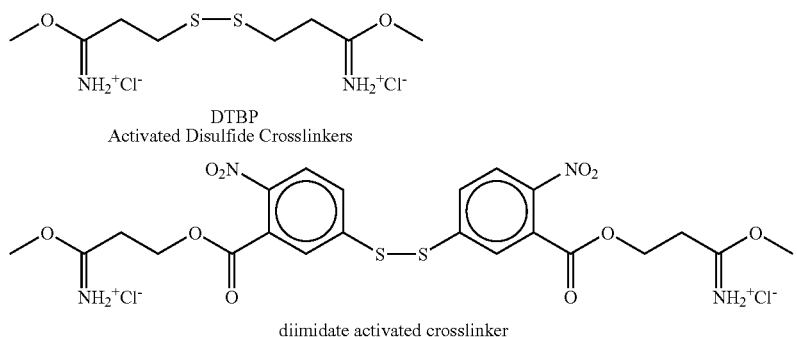

DTBP
Activated Disulfide Crosslinkers diimidate activated crosslinker

-continued

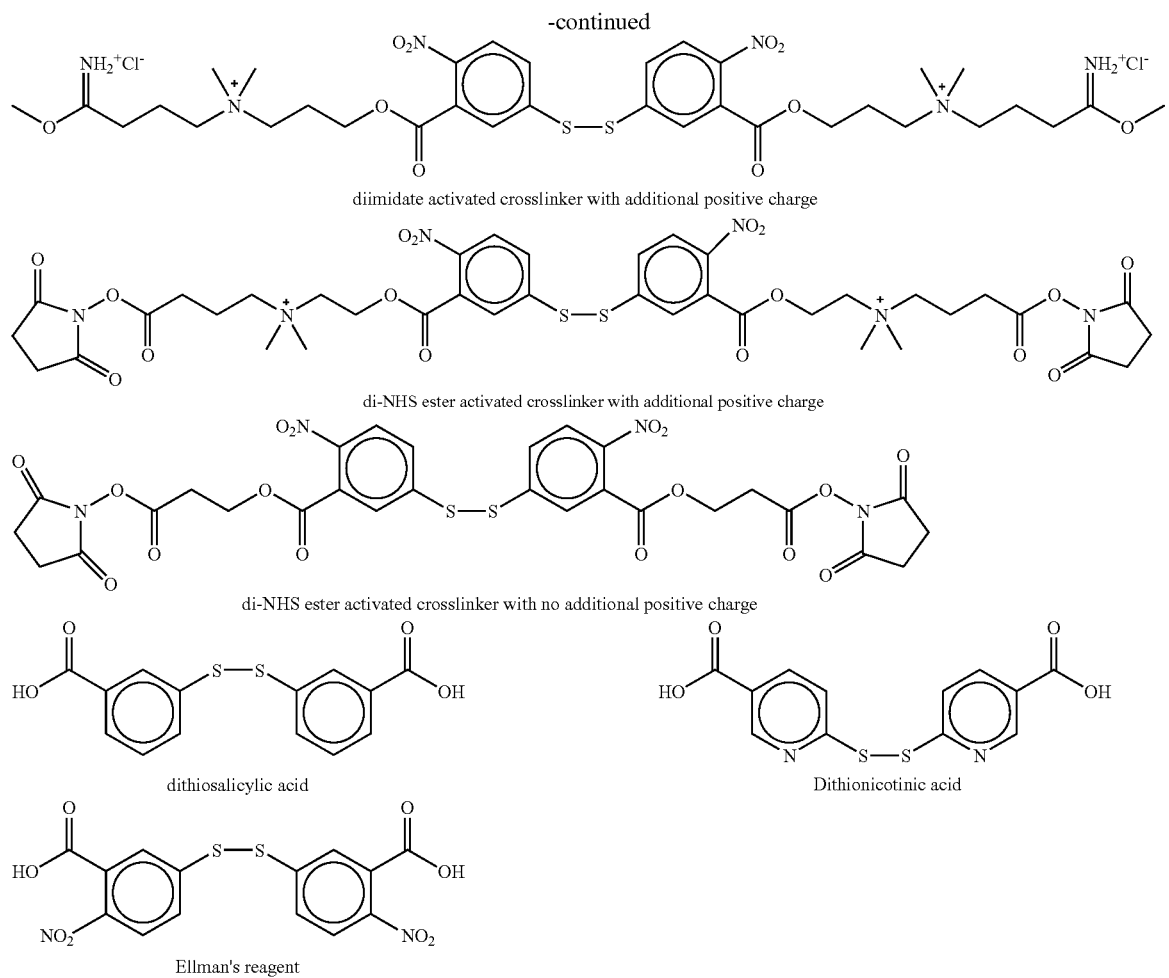

diimidate activated crosslinker with additional positive charge di-NHS ester activated crosslinker with additional positive charge di-NHS ester activated crosslinker with no additional positive charge dithiosalicylic acid Dithionicotinic acid Ellman's reagent The reduction potential can also be altered by proper choice of cationic co-monomer. For example when DTBP is polymerized along with diaminobutane the disulfide bond is reduced by DTT, but not glutathione. When ethylenediamine is polymerized with DTBP the disulfide bond is now reduced by glutathione. This is apparently due to the proximity of the disulfide bond to the amidine functionality in the bulk polymer.

The charge density of the bulk polymer can be controlled through choice of cationic monomer, or by incorporating positive charge into the disulfide co-monomer. For example spermine a molecule containing 4 amino groups spaced by 3-4-3 methylene groups could be used for the cationic monomer. Because of the spacing of the amino groups they would all bear positive charges in the bulk polymer with the exception of the end primary amino groups that would be derivitized during the polymerization. Another monomer that could be used is N,N'-bis(2-aminoethyl)-1,3-propediamine (AEPD) a molecule containing 4 amino groups spaced by 2-3-2 methylene groups. In this molecule the spacing of the amines would lead to less positive charge at physiological pH, however the molecule would exhibit pH sensitivity, that is bear different net positive charge, at different pH's. A molecule such as tetraethylenepentamine could also be used as the cationic monomer, this molecule consists of 5 amino groups each spaced by two methylene units. This molecule would give the bulk polymer pH sensitivity, due to the spacing of the amino groups as well as charge density, due to the number and spacing of the amino groups. The charge density can also be affected by incorporating positive charge into the disulfide containing monomer, or by using imidate groups as the reactive portions of the disulfide containing monomer as imidates are transformed into amidines upon reaction with amine which retain the positive charge.

The bulk polymer can be designed to allow further functionalization of the polymer by incorporating monomers with protected primary amino groups. These protected primary amines can then be deprotected and used to attach other functionalities such as nuclear localizing signals, endosome disrupting peptides, cell-specific ligands, fluorescent marker molecules, as a site of attachment for further crosslinking of the polymer to itself once it has been complexed with a polynucleic acid, or as a site of attachment for a second anionic layer when a cleavable polymer/polynucleic acid particle is being recharged to an anionic particle. An example of such a molecule is 3,3'-(N',N'''-tert-butoxycarbonyl)-N-(3'-trifluoroacetamidylpropane)-N-methyldipropylammonium bromide (see experimental), this molecule would be incorporated by removing the two BOC protecting groups, incorporating the deprotected monomer into the bulk polymer, followed by deprotection of the trifluoroacetamide protecting group.

Cleavable Anionic Polymers

Cleavable anionic polymers can be designed in much the same manner as the cationic polymers. Short, multi-valent oligopeptides of glutamic or aspartic acid can be synthesized with the carboxy terminus capped with ethylene diamine. This oligo can the be incorporated into a bulk polymer as a co-monomer with any of the amine reactive disulfide containing crosslinkers mentioned previously. A preferred crosslinker would make use of NHS esters as the reactive group to avoid retention of positive charge as occurs with imidates. The cleavable anionic polymers can be used to recharge positively charged particles of condensed polynucleic acids.

Examples of Cleavable Polymers

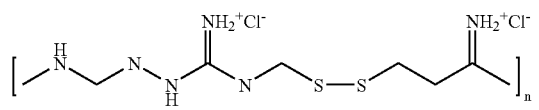

Co-ethylenediamine/DTBP cleavable cationic polymer

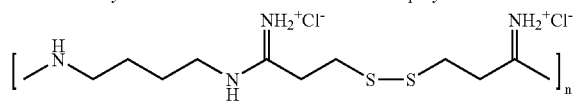

Co-diaminobutane/DTBP cleavable cationic polymer

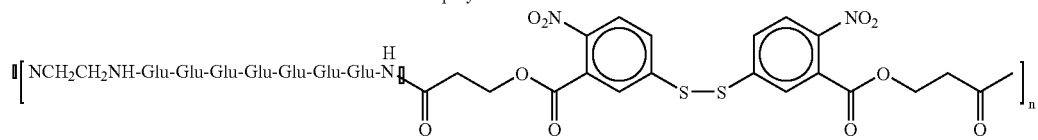

Co-glutamic acid/activated disulfide cleavable anionic polymer

The cleavable anionic polymers can have co-monomers incorporated to allow attachment of cell-specific ligands, endosome disrupting peptides, fluorescent marker molecules, as a site of attachment for further crosslinking of the polymer to itself once it has been complexed with a polynucleic acid, or as a site of attachment for to the initial cationic layer. For example the carboxyl groups on a portion of the anionic co-monomer could be coupled to an aminoalcohol such as 4-hydroxybutylamine. The resulting alcohol containing co-monomer can be incorporated into the bulk polymer at any ratio. The alcohol functionalities can then be oxidized to aldehydes, which can be coupled to amine containing ligands etc. in the presence of sodium cyanoborohydride via reductive amination.

pH Cleavable Polymers for Intracellular Compartment Release

A cellular transport step that has importance for gene transfer and drug delivery is that of release from intracellular compartments such as endosomes (early and late), lysosomes, phagosomes, vesicle, endoplasmic reticulum, Golgi apparatus, trans Golgi network (TGN), and sarcoplasmic reticulum. Release includes movement out of an intracellular compartment into cytoplasm or into an organelle such as the nucleus. Chemicals such as chloroquine, bafilomycin or Brefeldin A1. Chloroquine decreases the acidification of the endosomal and lysosomal compartments but also affects other cellular functions. Brefeldin A, an isoprenoid fungal metabolite, collapses reversibly the Golgi apparatus into the endoplasmic reticulum and the early endosomal compartment into the trans-Golgi network (TGN) to form tubules. Bafilomycin $A_1$, a macrolide antibiotic is a more specific inhibitor of endosomal acidification and vacuolar type $H^+$-ATPase than chloroquine. The ER-retaining signal (KDEL sequence) has been proposed to enhance delivery to the endoplasmic reticulum and prevent delivery to lysosomes.

To increase the stability of DNA particles in serum, we have added to positively-charged DNA/polycation particles polyanions that form a third layer in the DNA complex and make the particle negatively charged. To assist in the disruption of the DNA complexes, we have synthesized polymers that are cleaved in the acid conditions found in the endosome, pH 5-7. Cleavage of polymers in the DNA complexes in the endosome assists in endosome disruption and release of DNA into the cytoplasm.

There are two ways to cleave a polyion: cleavage of the polymer backbone resulting in smaller polyions and cleavage of the link between the polymer backbone and the ion containing groups resulting in small ionized molecules and a polymer. In either case, the interaction between the polyion and DNA is broken and the number of molecules in the endosome increases. This causes an osmotic shock to the endosomes and disrupts the endosomes. In the second case, if the polymer backbone is hydrophobic it may interact with the membrane of the endosome. Either effect may disrupt the endosome and thereby assist in release of DNA.

To construct cleavable polymers, one may attach the ions or polyions together with bonds that are inherently labile such as disulfide bonds, diols, diazo bonds, ester bonds, sulfone bonds, acetals, ketals, enol ethers, enol esters, imines, iminiums, and enamines. Another approach is construct the polymer in such a way as to put reactive groups, i.e. electrophiles and nucleophiles, in close proximity so that reaction between the function groups is rapid. Examples include having carboxylic acid derivatives (acids, esters, amides) and alcohols, thiols, carboxylic acids or amines in the same molecule reacting together to make esters, thiol esters, acid anhydrides or amides.

In one embodiment, ester acids and amide acids that are labile in acidic environments (pH less than 7, greater than 4) to form an alcohol and amine and an anhydride are use in a variety of molecules and polymers that include peptides, lipids, and multimolecular associations such as liposomes.

In one embodiment, ketals that are labile in acidic environments (pH less than 7, greater than 4) to form a diol and a ketone are use in a variety of molecules and polymers that include peptides, lipids, and liposomes.

In one embodiment, acetals that are labile in acidic environments (pH less than 7, greater than 4) to form a diol and an aldehyde are use in a variety of molecules and polymers that include peptides, lipids, and liposomes.

In one embodiment, enols that are labile in acidic environments (pH less than 7, greater than 4) to form a ketone and an alcohol are use in a variety of molecules and polymers that include peptides, lipids, and liposomes.

In one embodiment, iminiums that are labile in acidic environments (pH less than 7, greater than 4) to form an amine and an aldehyde or a ketone are use in a variety of molecules and polymers that include peptides, lipids, and liposomes.

pH-Sensitive Cleavage of Peptides and Polypeptides

In one embodiment, peptides and polypeptides (both referred to as peptides) are modified by an anhydride. The amine (lysine), alcohol (serine, threonine, tyrosine), and thiol (cysteine) groups of the peptides are modified by the an anhydride to produce an amide, ester or thioester acid. In the acidic environment of the internal vesicles (pH less than 6.5, greater than 4.5; early endosomes, late endosomes, or lysosome) the amide, ester, or thioester is cleaved displaying the original amine, alcohol, or thiol group and the anhydride.

A variety of endosomolytic and amphipathic peptides can be used in this embodiment. A positively-charged amphipathic/endosomolytic peptide is converted to a negatively-charged peptide by reaction with the anhydrides to form the amide acids and this compound is then complexed with a polycation-condensed nucleic acid. After entry into the endosomes, the amide acid is cleaved and the peptide becomes positively charged and is no longer complexed with the polycation-condensed nucleic acid and becomes amphipathic and endosomolytic. In one embodiment the peptides contains tyrosines and lysines. In yet another embodiment, the hydrophobic part of the peptide (after cleavage of the ester acid) is at one end of the peptide and the hydrophilic part (e.g. negatively charged after cleavage) is at another end. The hydrophobic part could be modified with a dimethylmaleic anhydride and the hydrophilic part could be modified with a citranconyl anhydride. Since the dimethylmaleyl group is cleaved more rapidly than the citrconyl group, the hydrophobic part forms first. In another embodiment the hydrophilic part forms alpha helixes or coil-coil structures.

Polynucleotide

The term nucleic acid is a term of art that refers to a string of at least two base-sugar-phosphate combinations. (A polynucleotide is distinguished from an oligonucleotide by containing more than 120 monomeric units.) Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus. Anti-sense is a polynucleotide that interferes with the function of DNA and/or RNA. The term nucleic acids- refers to a string of at least two base-sugar-phosphate combinations. Natural nucleic acids have a phosphate backbone, artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of an tRNA (transfer RNA), snRNA (small nuclear RNA), rRNA (ribosomal RNA), mRNA (messenger RNA), anti-sense RNA, and ribozymes. DNA may be in form plasmid DNA, viral DNA, linear DNA, or chromosomal DNA or derivatives of these groups. In addition these forms of DNA and RNA may be single, double, triple, or quadruple stranded. The term also includes PNAs (peptide nucleic acids), phosphorothioates, and other variants of the phosphate backbone of native nucleic acids.

DNA may be in form of cDNA, in vitro polymerized DNA, plasmid DNA, parts of a plasmid DNA, genetic material derived from a virus, linear DNA, expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. A polynucleotide may be single stranded or double stranded.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. The polynucleotide can be a sequence whose presence or expression in a cell alters the expression or function of cellular genes or RNA. A delivered polynucleotide can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Polynucleotides may contain an expression cassette coded to express a whole or partial protein, or RNA. An expression cassette refers to a natural or recombinantly produced polynucleotide that is capable of expressing a sequence. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences. The polynucleotide may contain sequences that do not serve a specific function in the target cell but are used in the generation of the polynucleotide. Such sequences include, but are not limited to, sequences required for replication or selection of the polynucleotide in a host organism.

A polynucleotide can be delivered to a cell to study gene function. Delivery of a polynucleotide to a cell can also have potential clinical applications. Clinical applications include treatment of muscle disorders or injury, circulatory disorders, endocrine disorders, immune modulation and vaccination, and metabolic disorders (Baumgartner et al. 1998, Blau et al. 1995, Svensson et al. 1996, Baumgartner et al. 1998, Vale et al. 2001, Simovic et al. 2001).

A transfection agent, or transfection reagent or delivery vehicle, is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, polycations, histone proteins, polyethylenimine, polylysine, and polyampholyte complexes. For delivery in vivo, complexes made with sub-neutralizing amounts of cationic transfection agent may be preferred. Non-viral vectors is include protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers).

The term naked nucleic acids indicates that the nucleic acids are not associated with a transfection reagent or other delivery vehicle that is required for the nucleic acid to be delivered to a target cell.

EXAMPLES

Example 1

Reporter Polynucleotides

The pCI-Luc-K expression vector was generated by ligating the CMV enhancer/promoter (pCI mammalian expression vector; Promega, Madison, Wis.) to the expression cassette of the firefly luciferase reporter gene (pSP-luc$^+$ expression vector—Promega) and replacing the ampicillin antibiotic resistance gene with the kanamycin antibiotic resistance gene. pCI-LacZ is similar to pCI-Luc-K and contained the β-galactosidase reporter gene under control of a cytomegalovirus enhancer/promoter. pCMV-hSEAP expresses human secreted alkaline phosphatase, hSEAP, from the cytomegalovirus enhancer/promoter. pMIR48 contains the firefly luciferase gene under control of the cytomegalovirus enhancer/promoter.

Reporter or marker genes, such as the genes for luciferase and β-galactosidase, serve as useful paradigms for expression of intracellular proteins in general. Similarly, reporter or marker genes, such as secreted alkaline phosphatase (SEAP) serve as useful paradigms for secreted proteins in general. Also, inhibition of reporter gene expression, such as following delivery of siRNA, indicate the reasonable probability of inhibiting other genes by delivering appropriate siRNA.

We have disclosed gene expression achieved from reporter genes in specific tissues. Levels of a gene product, including reporter (marker) gene products, are measured which then indicate a reasonable expectation of similar amounts of gene expression by transfecting other polynucleotides. Levels of treatment considered beneficial by a person having ordinary skill in the art differ from disease to disease, for example: Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes such as the genes for luciferase and β-galactosidase serve as useful paradigms for expression of intracellular proteins in general. Similarly, reporter or marker genes secreted alkaline phosphatase (SEAP) serve as useful paradigms for secreted proteins in general.

Example 2

Intravascular Injections of DNA/Labile Polymer Complexes

A. Synthesis of L-cystine-1,4-bis(3-aminopropyl)piperazine copolymer (M66): To a solution of L-cystine (1 g, 4.2 mmol, Aldrich Chemical Company) in acetone (10 ml) and water (10 ml) was added 2-(tert-butoxycarbonyloxyimino)-2-phenylacetonitrile (2.5 g, 10 mmol, Aldrich) and triethylamine (1.4 ml, 10 mmol, Aldrich) to yield N,N'-Bis(t-BOC)-L-cystine. The reaction was allowed to stir overnight at room temperature. The water and acetone was then removed by rotary evaporation resulting in a yellow solid. The diBOC compound was then isolated by flash chromatography on silica gel eluting with ethyl acetate 0.1% acetic acid. To a solution of N,N'-Bis(t-BOC)-L-cystine (85 mg, 0.15 mmol) in ethyl acetate (20 ml) was added N,N'-dicyclohexylcarbodiimide (108 mg, 0.5 mmol) and N-hyroxysuccinimide (60 mg, 0.5 mmol). After 2 hr, the solution was filtered through a cotton plug and 1,4-bis(3-aminopropyl)piperazine (54 µL, 0.25 mmol) was added. The reaction was allowed to stir at room temperature for 16 h. The ethyl acetate was then removed by rotary evaporation and the resulting solid was dissolved in trifluoroacetic acid (9.5 ml), water (0.5 ml) and triisopropylsilane (0.5 ml). After 2 h, the trifluoroacetic acid was removed by rotary evaporation and the aqueous solution was dialyzed in a 15,000 MW cutoff tubing against water (2×2 l) for 24 h. The solution was then removed from dialysis tubing, filtered through 5 µM nylon syringe filter and then dried by lyophilization to yield 30 mg of M66 polymer.

B. Synthesis of 5,5'-Dithiobis(2-nitrobenzoic acid)Pentaethylenehexamine Copolymer (M72): 5,5'-dithiobis(2-nitrobenzoic acid) (50.0 mg, 0.126 mmol, Aldrich) and N-hydroxysuccinimide (29.0 mg, 0.252 mmol, Aldrich) were taken up in 1.0 ml dichloromethane. Dicylohexyl-carbodiimide (52.0 mg, 0.252 mmol) was added and the reaction mixture was stirred overnight at room temperature. After 16 hr, the reaction mixture was partitioned in EtOAc/H$_2$O. The organic layer was washed 2×H$_2$O, 1× brine, dried (MgSO$_4$) and concentrated under reduced pressure. The residue was taken up in CH$_2$Cl$_2$, filtered, and purified by flash column chromatography on silica gel (130×30 mm, EtOAc:CH$_2$Cl$_2$ 1:9 eluent) to afford 42 mg (56%) 5,5'-dithiobis[succinimidyl(2-nitrobenzoate)] as a white solid, 5,5'-Dithiobis[succinimidyl(2-nitrobenzoate)]{H$^1$ NMR (DMSO) ∂7.81-7.77 (d, 2H), 7.57-7.26 (m, 4H), 3.69 (s, 8 H)}. Pentaethylene-hexamine (4.2 µL, 0.017 mmol, Aldrich) was taken up in 1.0 ml dichloromethane and HCl (1 ml, 1 M in Et$_2$O, Aldrich) was added Et$_2$O was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropyl-ethylamine (12 µL, 0.068 mmol, Aldrich) was added dropwise. After 16 hr, the solution was cooled, diluted with 3 ml H$_2$O, and dialyzed in 12,000-14,000 MW cutoff tubing against water (2×2 L) for 24 hr. The solution was then removed from dialysis tubing and dried by lyophilization to yield 5.9 mg (58%) of M72 polymer.

C. Increased pressure injection of pDNA/cationic polymer complexes (containing 10 µg of pCILuc; a luciferase expression vector utilizing the human CMV promoter) in 2.5 ml of Ringers solution (147 mM NaCl, 4 mM KCl, 1.13 mM CaCl$_2$) into the tail vein of ICR mice facilitated expression levels higher than comparable injections using naked plasmid DNA (pCILuc). Maximal luciferase expression using the tail vein approach was achieved when the DNA solution was injected within 7 seconds. Luciferase expression was also critically dependent on the total injection volume. High level gene expression in mice was obtained following tail vein injection of polynucleotide/polymer complexes of 1, 1.5, 2, 2.5, and 3 ml total volume. There is a positive correlation between injection volume and gene expression for total injection volumes over 1 ml. For the highest expression efficiencies an injection delivery rate of greater than 0.003 ml per gram (animal weight) per second is likely required. Injection rates of 0.004, 0.006, 0.009, 0.012 ml per gram (animal weight) per second yield successively greater gene expression levels.

Figure 1A:
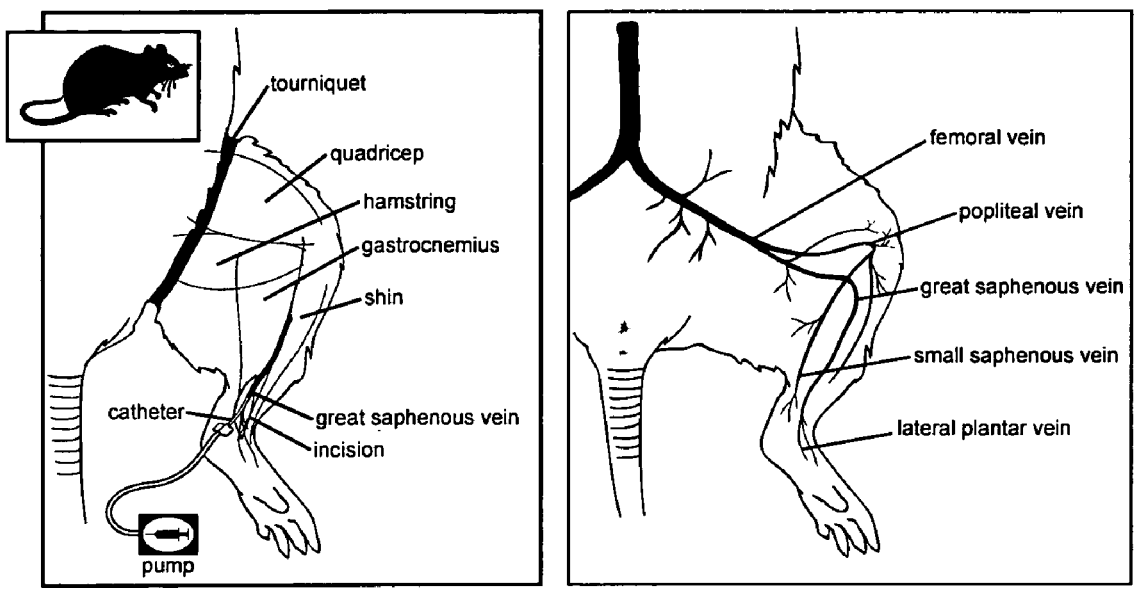
FIG. 1A-1D. Schematic diagram of catheter-mediated intravenous injection of nucleic acids into mammalian limb A) IV delivery to distal hind limb of rats. B) IV delivery to distal hind limb of dog. C) IV delivery to distal hind limb of primate. D) IV delivery to distal hind limb of human. Left panel in each illustrates major veins of the limb. Occlusion sites and injection sites shown in the diagrams are for illustrative purposes. Different occlusion and injection sites are possible as indicated in the description and examples.
Figure 1B:
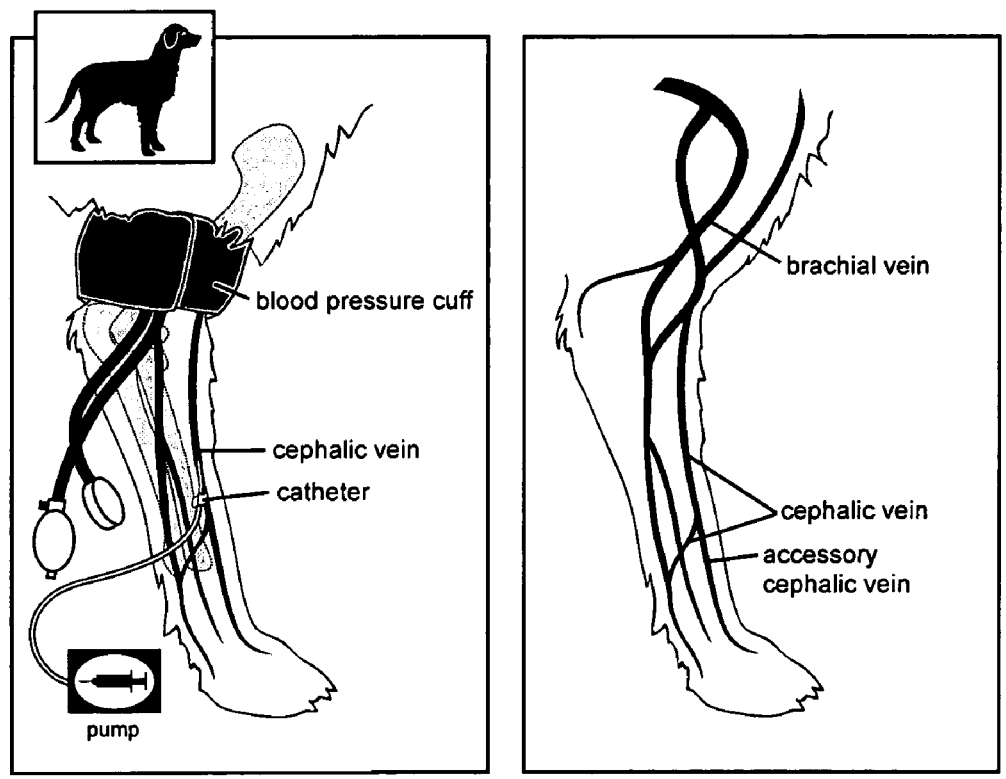
Figure 1C:
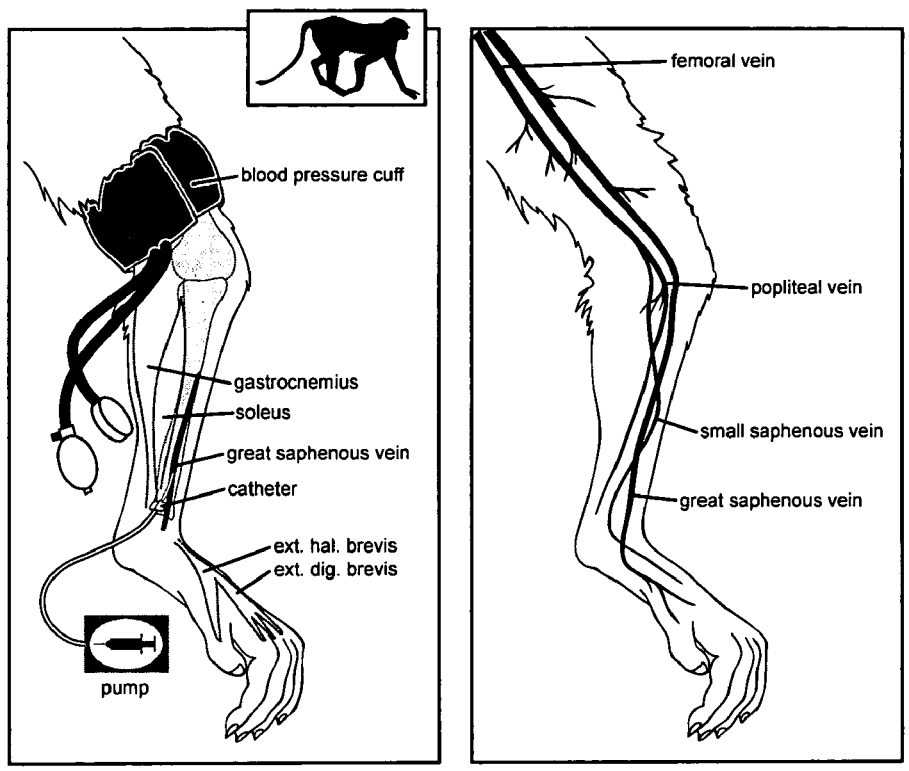
Figure 1D:
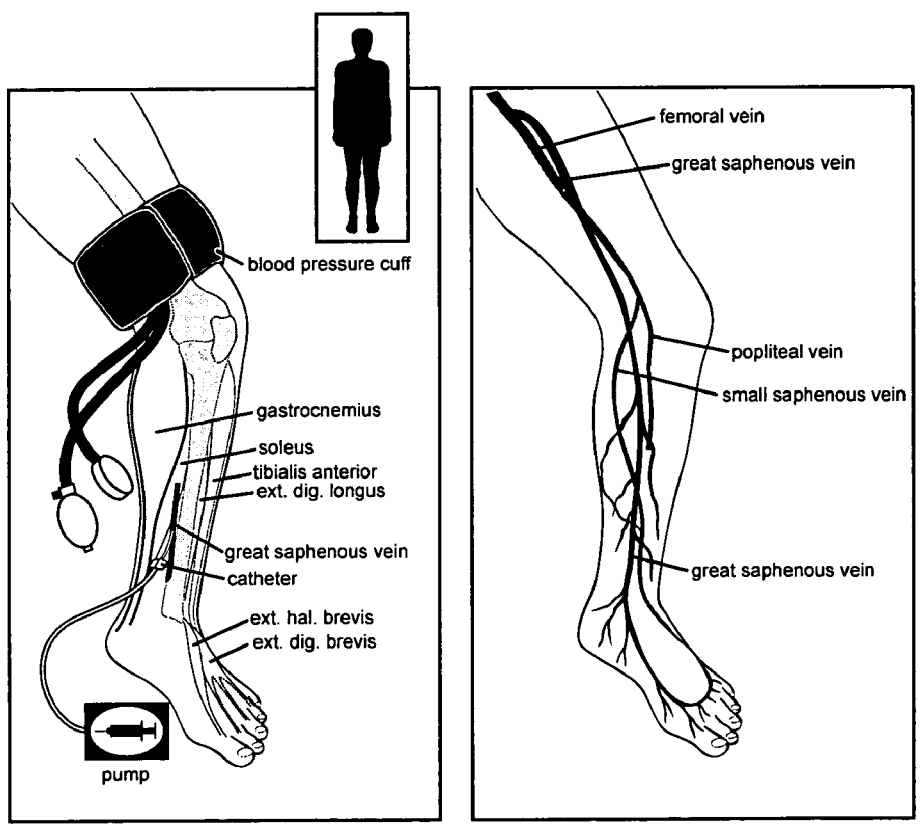
Figure 2:
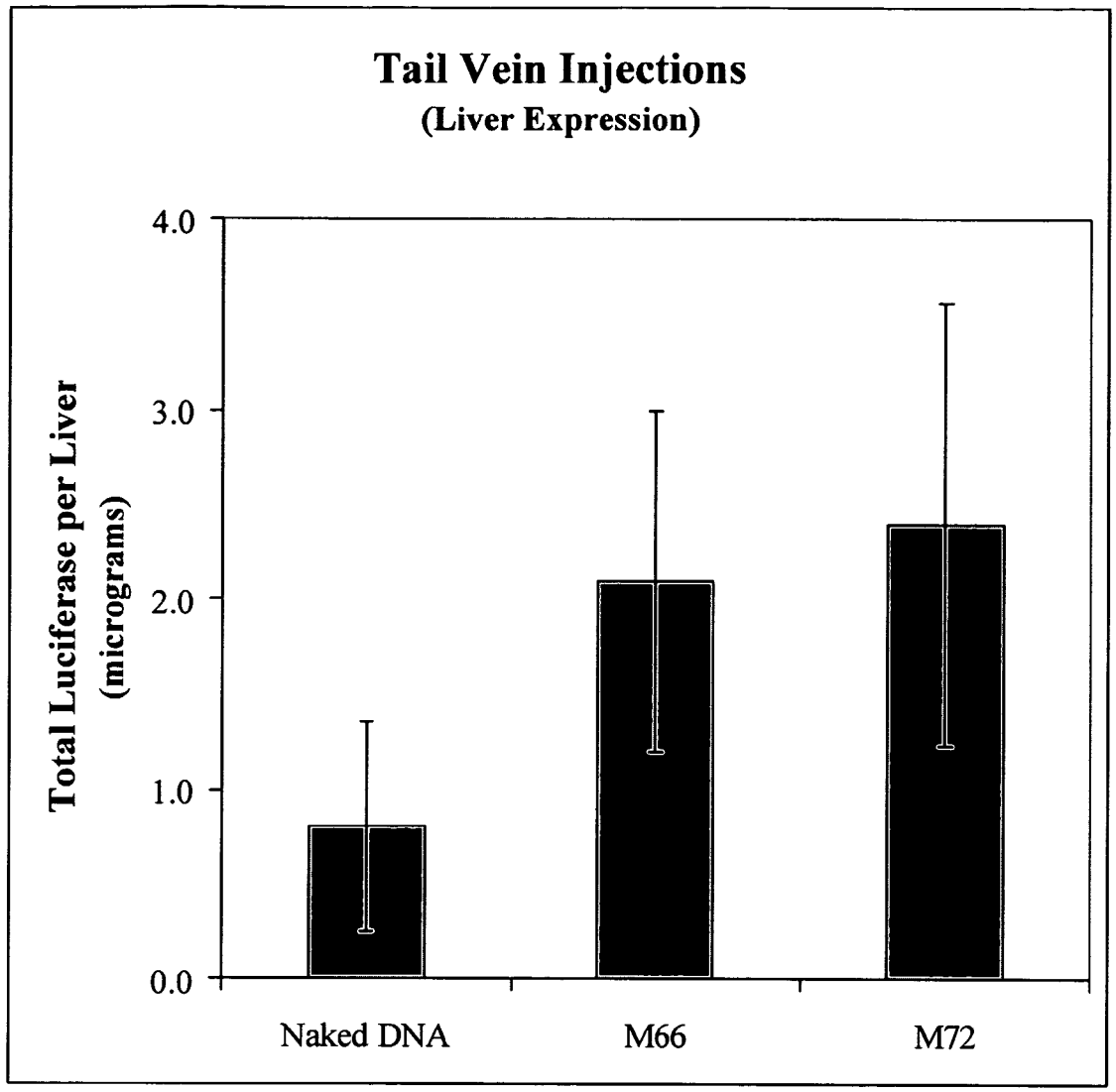
FIG. 2 Graph illustrating high level luciferase expression in liver following tail vein injections of naked plasmid DNA and plasmid DNA complexed with labile disulfide containing polycations.

FIG. 2 illustrates high level luciferase expression in liver following tail vein injections of naked plasmid DNA and plasmid DNA complexed with labile disulfide containing polycations M66 and M72. The labile polycations were complexed with DNA at a 3:1 wt:wt ratio resulting in a positively charged complex. Complexes were injected into 25 gram ICR mice in a total volume of 2.5 ml of Ringer's solution.

Figure 3:
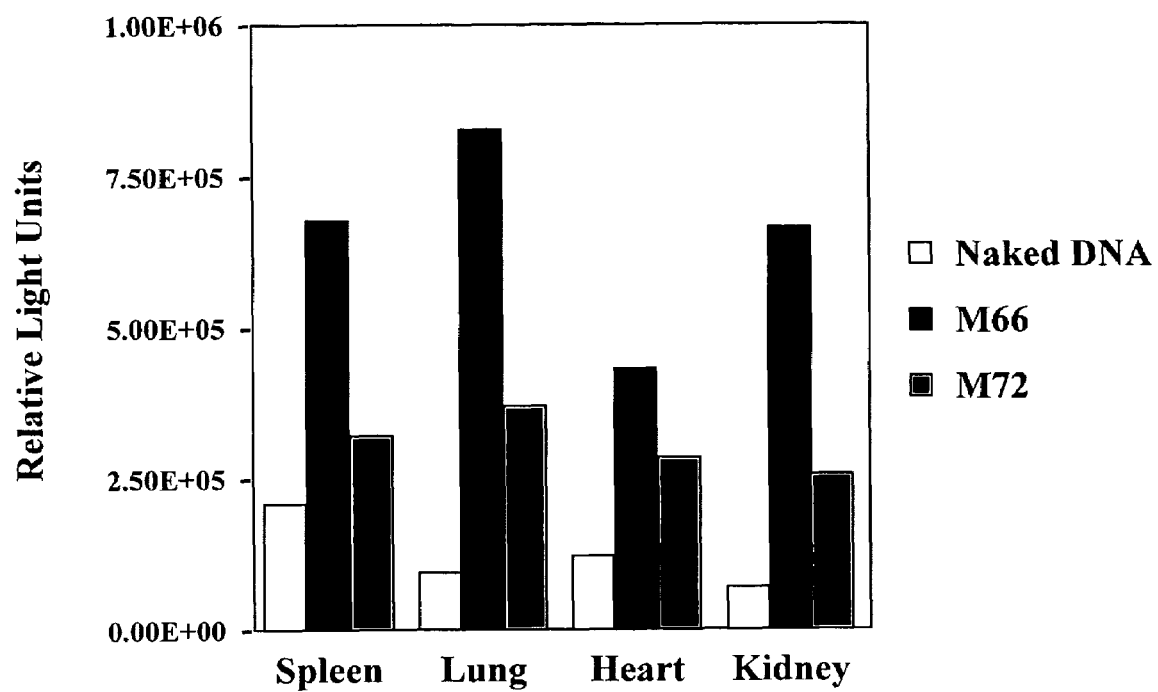
FIG. 3. Graph indicating high level luciferase expression in spleen, lung, heart and kidney following tail vein injections of naked plasmid DNA and plasmid DNA complexed with labile disulfide containing polycations.

FIG. 3 indicates high level luciferase expression in spleen, lung, heart and kidney following tail vein injections of naked plasmid DNA and plasmid DNA complexed with labile disulfide containing polycations M66 and M72. The labile polycations were complexed with DNA at a 3:1 wt:wt ratio resulting in a positively charged complex. Complexes were injected into 25 gram ICR mice in a total volume of 2.5 ml of Ringer's solution.

D. Injection of plasmid DNA (pCILuc)/M66 complexes into the iliac artery of rats: 500 µg pDNA (500 µl) was mixed with M66 polymer at a 1:3 wt:wt ratio in 500 µl saline. Complexes were then diluted in Ringers solution to total volume of 10 mls. The complexes in 10 mls Ringer's were injected into the iliac artery of Sprague-Dawley rats (Harlan, Indianapolis, Ind.) in approximately 10 seconds. Animals were sacrificed after 1 week and individual muscle groups were removed and assayed for luciferase expression. These results indicate that high level gene expression in all muscle groups of the leg was facilitated by intravascular delivery of pCILuc/M66 complexes into rat iliac artery.

| Hind Limb Muscle Group | Relative Light Units total | ng Luciferase |
|---|---|---|
| upper leg posterior | $6.46 \times 10^8$ | 32 |
| upper leg anterior | $3.58 \times 10^9$ | 183 |
| upper leg middle | $2.63 \times 10^9$ | 134 |
| lower leg anterior | $3.19 \times 10^9$ | 163 |
| lower leg anterior | $1.97 \times 10^9$ | 101 |

Example 3

A. Synthesis of 5,5'-Dithiobis(2-nitrobenzoic acid)-Tetraethylenepentamine Copolymer (M57): Tetraethylenepentamine (3.2 µL, 0.017 mmol, Aldrich) was taken up in 1.0 ml dichloromethane and HCl (1 ml, 1 M in Et$_2$O, Aldrich) was added Et$_2$O was added and the resulting HCl salt was collected by filtration. The salt was taken up in 1 ml DMF and 5,5'-dithiobis[succinimidyl (2-nitrobenzoate)] (10 mg, 0.017 mmol) was added. The resulting solution was heated to 80° C. mmol) and diisopropylethylamine (15 µL, 0.085 mmol, Aldrich) was added dropwise. After 16 hr, the solution was cooled, diluted with 3 ml H$_2$O, and dialyzed in 12,000-14,000 MW cutoff tubing against water (2×2 L) for 24 h. The solution was then removed from dialysis tubing and dried by lyophilization to yield 5.8 mg (62%) of 5,5'-dithiobis(2-nitrobenzoic acid)-tetraethylenepentamine copolymer.

B. Mouse Tail Vein Injections of pDNA (pCI Luc)/M57 polymer Complexes:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300 µL DMSO then M57 polymer (336 µg) was added followed by 2.5 ml Ringers.

Hydrodynamic (2.5 ml) tail vein injections of the complex were performed as previously described (Zhang G et al. 1999). Results reported are for liver expression, and are the average of two mice. Luciferase expression was determined as previously reported (Wolff J A et al. 1990) A Lumat LB 9507 (EG&G Berthold, Bad-Wildbad, Germany) luminometer was used. Results indicate that pDNA (pCI Luc)/M57 polymer complexes are nearly equivalent to pCI Luc DNA itself in hydrodynamic injections. This indicates that the pDNA is being released from the complex and is accessible for transcription.

| Results | Luciferase Expression (RLUs) |
|---|---|
| Complex I: | 25,200,000 |
| Complex II: | 21,000,000 |

Example 4

A. Synthesis of 5,5'-Dithiobis(2-nitrobenzoic acid)-Tetraethylenepentamine-Tris(2-aminoethyl)amine Copolymer (M58): Tetraethylenepentamine (2.3 µL, 0.012 mmol, Aldrich) and tris(2-aminoethyl)amine (0.51 µL, 0.0034 mmol, Aldrich) were taken up in 0.5 ml methanol and HCl (1 ml, 1 M in $Et_2O$, Aldrich) was added. $Et_2O$ was added and the resulting HCl salt was collected by filtration. The salt was taken up in 1 ml DMF and 5,5'-dithiobis-[succinimidyl(2-nitrobenzoate)] (10 mg, 0.017 mmol) was added. The resulting solution was heated to 80° C. and diisopropylethylamine (15 µL, 0.085 mmol, Aldrich) was added dropwise. After 16 hr, the solution was cooled, diluted with 3 ml $H_2O$, and dialyzed in 12,000-14,000 MW cutoff tubing against water (2×2 L) for 24 h. The solution was then removed from dialysis tubing and dried by lyophilization to yield 6.9 mg (77%) of M58 polymer.

B. Mouse Tail Vein Injections of pDNA (pCI Luc)/M58 polymer:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300 µL DMSO then M58 polymer (324 µg) was added followed by 2.5 ml Ringers.

Tail vein injections (2.5 ml) of the complex were performed as previously described. Results reported are for liver expression, and are the average of two mice. Luciferase expression was determined a previously shown. Results indicate that pDNA (pCI Luc)/M58 Complexes are more effective than injection of naked DNA. This indicates that the pDNA is being released from the complex and is accessible for transcription.

| Results | Luciferase Expression (RLUs) |
|---|---|
| Complex I: | 25,200,000 |
| Complex II: | 37,200,000 |

Example 5

A. Synthesis of 5,5'-Dithiobis(2-nitrobenzoic acid)-N,N'-Bis(2-aminoethyl)-1,3-propanediamine Copolymer (M59): N,N'-Bis(2-aminoethyl)-1,3-propanediamine (2.8 µL, 0.017 mmol, Aldrich) was taken up in 1.0 ml dichloromethane and HCl (1 ml, 1 M in $Et_2O$, Aldrich) was added. $Et_2O$ was added and the resulting HCl salt was collected by filtration. The salt was taken up in 1 ml DMF and 5,5'-dithiobis[succinimidyl (2-nitrobenzoate)] (10 mg, 0.017 mmol) was added. The resulting solution was heated to 80° C. and diisopropylethylamine (12 µL, 0.068 mmol, Aldrich) was added dropwise. After 16 hr, the solution was cooled, diluted with 3 ml $H_2O$, and dialyzed in 12,000-14,000 MW cutoff tubing against water (2×2 L) for 24 hr. The solution was then removed from dialysis tubing and dried by lyophilization to yield 5.9 mg (66%) of M59 polymer.

B. Mouse Tail Vein Injections of pDNA (pCI Luc)/M59:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300 µL DMSO then M59 polymer (474 µg) was added followed by 2.5 ml Ringers.

Tail vein injections of 2.5 ml of the complex were performed as previously described. Results reported are for liver expression, and are the average of two mice. Luciferase expression was determined as previously shown. Results indicate that pDNA (pCI Luc)/M59 Complexes are less effective than naked DNA. Although the complex was less effective, the luciferase expression indicates that the pDNA is being released from the complex and is accessible for transcription.

| Results | Luciferase Expression (RLUs) |
|---|---|
| Complex I | 25,200,000 |
| Complex II | 341,000 |

Example 6

A. Synthesis of 5,5'-Dithiobis(2-nitrobenzoic acid)-N,N'-Bis(2-aminoethyl)-1,3-propanediamine-Tris(2-aminoethyl) amine Copolymer (M60): N,N'-Bis(2-aminoethyl)-1,3-propanediamine(2.0 µL, 0.012 mmol, Aldrich) and tris(2-aminoethyl)amine (0.51 µL, 0.0034 mmol, Aldrich) were taken up in 0.5 ml methanol and HCl (1 ml, 1 M in $Et_2O$, Aldrich) was added. $Et_2O$ was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropylethylamine (12 µL, 0.068 mmol, Aldrich) was added dropwise. After 16 hr, the solution was cooled, diluted with 3 ml $H_2O$, and dialyzed in 12,000-14,000 MW cutoff tubing against water (2×2 L) for 24 hr. The solution was then removed from dialysis tubing and dried by lyophilization to yield 6.0 mg (70%) of M60 polymer.

B. Mouse Tail Vein Injections of pDNA (pCI Luc)/M60 Copolymer Complexes:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300 µL DMSO then M60 polymer (474 µg) was added followed by 2.5 ml Ringers.

Tail vein injections of 2.5 ml of the complex were preformed as previously described. Results reported are for liver expression, and are the average of two mice. Luciferase expression was determined as previously shown. Results indicate that pDNA (pCI Luc)/M60 Copolymer Complexes are less effective than naked DNA. Although the complex was less effective, the luciferase expression indicates that the pDNA is being released from the complex and is accessible for transcription.

| Results | Luciferase Expression (RLUs) |
|---|---|
| Complex I | 25,200,000 |
| Complex II | 1,440,000 |

Example 7

A. Synthesis of L-cystine-1,4-bis(3-aminopropyl)piperazine copolymer (M67): To a solution of cystine (1 g, 4.2 mmol) in ammonium hydroxide (10 ml) in a screw-capped vial was added O-methylisourea hydrogen sulfate (1.8 g, 10 mmol). The vial was sealed and heated to 60° C. for 16 h. The solution was then cooled and the ammonium hydroxide was removed by rotary evaporation. The solid was then dissolved in water (20 ml), filtered through a cotton plug. The product was then isolated by ion exchange chromatography using Bio-Rex 70 resin and eluting with hydrochloric acid (100 mM).

B. Synthesis of guanidino-L-cystine1,4-bis(3-aminopropyl)piperazine copolymer: To a solution of guanidino-L-cystine (64 mg, 0.2 mmol) in water (10 ml) was slowly added N,N'-dicyclohexylcarbodiimide (82 mg, 0.4 mmol) and N-hyroxysuccinimide (46 mg, 0.4 mmol) in dioxane (5 ml). After 16 hr, the solution was filtered through a cotton plug and 1,4-bis(3-aminopropyl)piperazine (40 μL, 0.2 mmol) was added. The reaction was allowed to stir at room temperature for 16 h and then the aqueous solution was dialyzed in a 15,000 MW cutoff tubing against water (2×2 l) for 24 h. The solution was then removed from dialysis tubing, filtered through 5 μM nylon syringe filter and then dried by lyophilization to yield 5 mg of polymer.

C. Particle size of pDNA/M67 polymer and DNA/guanidino-L-cystine1,4-bis(3-aminopropyl)piperazine polymer complexes: To a solution of pDNA (10 μg/ml) in 0.5 ml 25 mM HEPES buffer pH 7.5 was added 10 μg/ml M67 polymer or guanidino-L-cystine1,4-bis(3-aminopropyl)piperazine polymer. The size of the complexes between DNA and the polymers were measured. For both polymers, the size of the particles were approximately 60 nm.

D. Condensation of DNA with M67 polymer and decondensation of DNA upon addition of glutathione: Fluorescein labeled DNA was used for the determination of DNA condensation in complexes with M67 polymer. pDNA was modified to a level of 1 fluorescein per 100 bases using Mirus' LabelIT Fluorescein kit. The fluorescence was determined using a fluorescence spectrophotometer (Shimadzu RF-1501 spectrofluorometer) at an excitation wavelength of 495 nm and an emission wavelength of 530 nm (Trubetskoy V S et al. Anal Biochem 1999 Vol 267 pp. 309-13, incorporated herein by reference). The intensity of the fluorescence of the fluorescein-labeled DNA (10 μg/ml) in 0.5 ml of 25 mM HEPES buffer pH 7.5 was 300 units. Upon addition of 10 μg/ml of M67 polymer, the intensity decreased to 100 units. To this DNA-polycation sample was added 1 mM glutathione and the intensity of the fluorescence was measured. An increase in intensity was measured to the level observed for the DNA sample alone. The half life of this increase in fluorescence was 8 minutes. The experiment indicates that DNA complexes with physiologically-labile disulfide-containing polymers are cleavable in the presence of the biological reductant glutathione.

E. Mouse Tail Vein Injection of DNA/M67 polymer and DNA/guanidino-L-cystine1,4-bis(3-aminopropyl)piperazine polymer Complexes: Plasmid delivery in the tail vein of ICR mice was performed as previously described. To pCILuc DNA (50 μg) in 2.5 ml H$_2$O was added either M67 polymer, guanidino-L-cystine1,4-bis(3-aminopropyl)piperazine polymer, or poly-L-lysine (34,000 MW, Sigma Chemical Company) (50 μg). The samples were then injected into the tail vein of mice using a 30 gauge, 0.5 inch needle. One day after injection, the animal was sacrificed, and a luciferase assay was conducted. The experiment indicates that DNA complexes with the physiologically-labile disulfide-containing polymers are capable of being broken, thereby allowing the luciferase gene to be expressed.

| Polycation | Luciferase Expression (ng) |
|---|---|
| poly-L-lysine | 6.2 |
| M67 | 439 |
| guanidino-L-cystine1,4-bis(3-aminopropyl)piperazine | 487 |

Example 8

A. Synthesis of citraconylpolyvinylphenol: Polyvinylphenol (10 mg 30,000 MW Aldrich) was dissolved in 1 ml anhydrous pyridine. To this solution was added citraconic anhydride (100 μL, 1 mmol) and the solution was allowed to react for 16 hr. The solution was then dissolved in 5 ml of aqueous potassium carbonate (100 mM) and dialyzed three times against 2 L water that was at pH8 with addition of potassium carbonate. The solution was then concentrated by lyophilization to 10 mg/ml of citraconylpolyvinylphenol.

B. Synthesis of citraconylpoly-L-tyrosine: Poly-L-tyrosine (10 mg, 40,000 MW Sigma) was dissolved in 1 ml anhydrous pyridine. To this solution was added citraconic anhydride (100 μL, 1 mmol) and the solution was allowed to react for 16 hr. The solution was then dissolved in 5 ml of aqueous potassium carbonate (100 mM) and dialyzed against 3×2 L water that was at pH 8 with addition of potassium carbonate. The solution was then concentrated by lyophilization to 10 mg/ml of citraconylpoly-L-tyrosine.

C. Synthesis of citraconylpoly-L-lysine: Poly-L-lysine (10 mg 34,000 MW Sigma) was dissolved in 1 ml of aqueous potassium carbonate (100 mM). To this solution was added citraconic anhydride (100 μL, 1 mmol) and the solution was allowed to react for 2 hr. The solution was then dissolved in 5 ml of aqueous potassium carbonate (100 mM) and dialyzed against 3×2 L water that was at pH8 with addition of potassium carbonate. The solution was then concentrated by lyophilization to 10 mg/ml of citraconylpoly-L-lysine.

D. Synthesis of dimethylmaleylpoly-L-lysine: Poly-L-lysine (10 mg 34,000 MW Sigma) was dissolved in 1 ml of aqueous potassium carbonate (100 mM). To this solution was added 2,3-dimethylmaleic anhydride (100 mg, 1 mmol) and the solution was allowed to react for 2 hr. The solution was then dissolved in 5 ml of aqueous potassium carbonate (100 mM) and dialyzed against 3×2 L water that was at pH8 with addition of potassium carbonate. The solution was then concentrated by lyophilization to 10 mg/ml of dimethylmaleylpoly-L-lysine.

E. Characterization of Particles Formed with citraconylated and dimethylmaleylated polymers: To a complex of DNA (20 μg/ml) and poly-L-lysine (40 μg/ml) in 1.5 ml was added the various citraconylpolyvinylphenol and citraconylpoly-L-lysine (150 μg/ml). The sizes of the particles formed were measured to be 90-120 nm and the zeta potentials of the particles were measured to be −10 to −30 mV (Brookhaven ZetaPlus Particle Sizer). To each sample was added acetic acid to make the pH 5. The size of the particles was measured as a function of time. Both citraconylpolyvinylphenol and citraconylpoly-L-lysine DNA complexes were unstable under acid pH. The citraconylpolyvinylphenol sample had particles >1 μm in 5 minutes and citraconylpoly-L-lysine sample had particles >1 μm in 30 minutes.

Example 9

A. Synthesis of Ketal from Polyvinylphenyl Ketone and Glycerol: Polyvinyl phenyl ketone (500 mg, 3.78 mmol, Aldrich) was taken up in 20 ml dichloromethane. Glycerol (304 µL, 4.16 mmol, Acros Chemical Company) was added followed by p-toluenesulfonic acid monohydrate (108 mg, 0.57 mmol, Aldrich). Dioxane (10 ml) was added and the solution was stirred at room temperature overnight. After 16 hrs, TLC indicated the presence of ketone. The solution was concentrated under reduced pressure, and the residue redissolved in DMF (7 ml). The solution was heated to 60° C. for 16 hrs. Dialysis against $H_2O$ (1×3 L, 3500 MWCO), followed by Lyophilization resulted in 606 mg (78%) of the ketal.

B. Synthesis of Ketal Acid of Polyvinylphenyl Ketone and Glycerol Ketal: The ketal from polyvinylphenyl ketone and glycerol (220 mg, 1.07 mmol) was taken up in dichloromethane (5 ml). Succinic anhydride (161 mg, 1.6 mmol, Sigma) was added followed by diisopropylethyl amine (0.37 ml, 2.1 mmol, Aldrich) and the solution was heated at reflux. After 16 hrs, the solution was concentrated, dialyzed against $H_2O$ (1×3 L, 3500 MWCO), and lyophilized to afford 250 mg (75%) of the ketal acid.

C. Particle Sizing and Acid Lability of Poly-L-Lysine/ Ketal Acid of Polyvinylphenyl Ketone and Glycerol Ketal Complexes: Particle sizing (Brookhaven Instruments Corporation, ZetaPlus Particle Sizer, I90, 532 nm) indicated an effective diameter of 172 nm (40 µg) for the ketal acid Addition of acetic acid to a pH of 5 followed by particle sizing indicated a increase in particle size to 84000. A poly-L-lysine/ ketal acid (40 µg, 1:3 charge ratio) sample indicated a particle size of 142 nm. Addition of acetic acid (5 µL, 6 N) followed by mixing and particle sizing indicated an effective diameter of 1970 nm. This solution was heated at 40° C. particle sizing indicated a effective diameter of 74000 and a decrease in particle counts. The particle sizer data indicates the loss of particles upon the addition of acetic acid to the mixture.

D. Synthesis of Ketal from Polyvinyl Alcohol and 4-Acetylbutyric Acid: Polyvinylalcohol (200 mg, 4.54 mmol, 30,000-60,000 MW, Aldrich) was taken up in dioxane (10 ml). 4-acetylbutyric acid (271 µL, 2.27 mmol, Aldrich) was added followed by p-toluenesulfonic acid monohydrate (86 mg, 0.45 mmol, Aldrich). After 16 hrs, TLC indicated the presence of ketone. The solution was concentrated under reduced pressure, and the residue redissolved in DMF (7 ml). The solution was heated to 60° C. for 16 hrs. Dialysis against $H_2O$ (1×4 L, 3500 MWCO), followed by lyophilization resulted in 145 mg (32%) of the ketal.

E. Particle Sizing and Acid Lability of Poly-L-Lysine/ Ketal from Polyvinyl Alcohol and 4-Acetylbutyric Acid Complexes: Particle sizing (Brookhaven Instruments Corporation, ZetaPlus Particle Sizer, I90, 532 nm) indicated an effective diameter of 280 nm (743 kcps) for poly-L-lysine/ ketal from polyvinyl alcohol and 4-acetylbutyric acid complexes (1:3 charge ratio). A poly-L-lysine sample indicated no particle formation. Similarly, a ketal from polyvinyl alcohol and 4-acetylbutyric acid sample indicated no particle formation. Acetic acid was added to the poly-L-lysine/ketal from polyvinyl alcohol and 4-acetylbutyric acid complexes to a pH of 4.5. Particle sizing indicated particles of 100 nm, but at a minimal count rate (9.2 kcps). The particle sizer data indicates the loss of particles upon the addition of acetic acid to the mixture.

Example 10

A. Synthesis of 1,4-Bis(3-aminopropyl)piperazine Glutaric Dialdehyde Copolymer (M140): 1,4-Bis(3-aminopropyl)piperazine (206 µL, 0.998 mmol, Aldrich) was taken up in 5.0 ml $H_2O$. Glutaric dialdehyde (206 µL, 0.998 mmol, Aldrich) was added and the solution was stirred at RT. After 30 min, an additional portion of $H_2O$ was added (20 ml), and the mixture neutralized with 6 N HCl to pH 7, resulting in a red solution. Dialysis against $H_2O$ (3×3 L, 12,000-14,000 MW cutoff tubing) and lyophilization afforded 38 mg (14%) of the copolymer B. Particle Sizing and Acid Lability of pDNA (pCI Luc)/ M140: To 50 µg pDNA in 2 ml HEPES (25 mM, pH 7.8) was added 135 µg M140 polymer. Particle sizing (Brookhaven Instruments Corporation, ZetaPlus Particle Sizer, I90, 532 nm) indicated an effective diameter of 110 nm for the complex. A 50 µg pDNA in 2 ml HEPES (25 mM, pH 7.8) sample indicated no particle formation. Similarly, a 135 µg M140 polymer in 2 ml HEPES (25 mM, pH 7.8) sample indicated no particle formation. Acetic acid was added to the pDNA (pCI Luc)/M140 complexes to a pH of 4.5. Particle sizing indicated particles of 2888 nm, and aggregation was observed. M140 polymer condenses pDNA, forming small particles. Upon acidification, the particle size increases, and aggregation occurs, indicating cleavage of the polymeric imine.

C. Mouse Tail Vein Injections of pDNA (pCILuc)/M140 polymer Complexes

Three complexes were prepared as follows:

Complex I: pDNA (pCI Luc, 50 µg) in 12.5 ml Ringers.

Complex II: pDNA (pCI Luc, 50 µg) was mixed with M140 polymer (50 µg) in 1.25 ml HEPES 25 mM, pH 8. This solution was then added to 11.25 ml Ringers.

Complex III: pDNA (pCI Luc, 50 µg) was mixed with poly-L-lysine (94.5 µg, MW 42,000, Sigma) in 12.5 ml Ringers.

2.5 ml tail vein injections of 2.5 ml of the complex were preformed as previously described. Luciferase expression was determined as previously indicated. Results indicate an increased level of pCI Luc DNA expression in pDNA/M140 complexes over pCI Luc DNA/poly-L-lysine complexes. These results also indicate that the pDNA is being released from the pDNA/M140 complexes, and is accessible for transcription.

| Results | Luciferase Expression (RLUs) |
| --- | --- |
| Complex I | 3,692,000 |
| Complex II | 1,047,000 |
| Complex III | 4,379 |

Example 11

Negatively Charged Complexes Using Non-Cleavable Polymers:

Many cationic polymers such as histone (H1, H2a, H2b, H3, H4, H5), HMG proteins, poly-L-lysine, polyethylenimine, protamine, and poly-histidine are used to compact polynucleic acids to help facilitate gene delivery in vitro and in vivo. A key for efficient gene delivery using prior art methods is that the non-cleavable cationic polymers (both in vitro and in vivo) must be present in a charge excess over the DNA so that the overall net charge of the DNA/polycation complex is positive. Conversely, using our intravascular delivery process having non-cleavable cationic polymer/DNA complexes we found that gene expression is most efficient when the overall net charge of the complexes are negative (DNA negative charge>polycation positive charge). Tail vein injections using cationic polymers commonly used for DNA condensation and in vitro gene delivery revealed that high gene expression occurred when the net charge of the complexes were negative.

The net surface charge of DNA/polymer particles formed at two different polymer to DNA ratios was determined by zeta potential analysis. DNA/polymer complexes were formed by mixing the components at the indicated charge:charge ratios in 25 mM HEPES, pH 8 at a DNA concentration of 20 micrograms per ml (pCILuc). Complexes were assayed for zeta potential on a Brookhaven ZetaPlus dynamic light scattering particle sizer/zeta potential analyzer. Both negative (0.5:1 ratio) and positive particles (5:1 ratio) should be theoretically obtained. Zeta potential analysis of these particles confirmed that the two different ratios did yield oppositely charged particles.

| Polycation | Polycation:DNA charge ratio | Surface Charge |
|---|---|---|
| Poly-L-lysine | 0.5:1 | −16.77 mV (n = 7) |
|  | 5.0:1 | +24.11 mV (n = 6) |
| Polyethylenimine | 0.5:1 | −12.47 mV (n = 7) |
|  | 5.0:1 | +35.74 mV (n = 8) |
| Histone | 0.5:1 | −9.60 mV (n = 8) |
|  | 5.0:1 | +20.97 mV (n = 8) |

Figure 4:
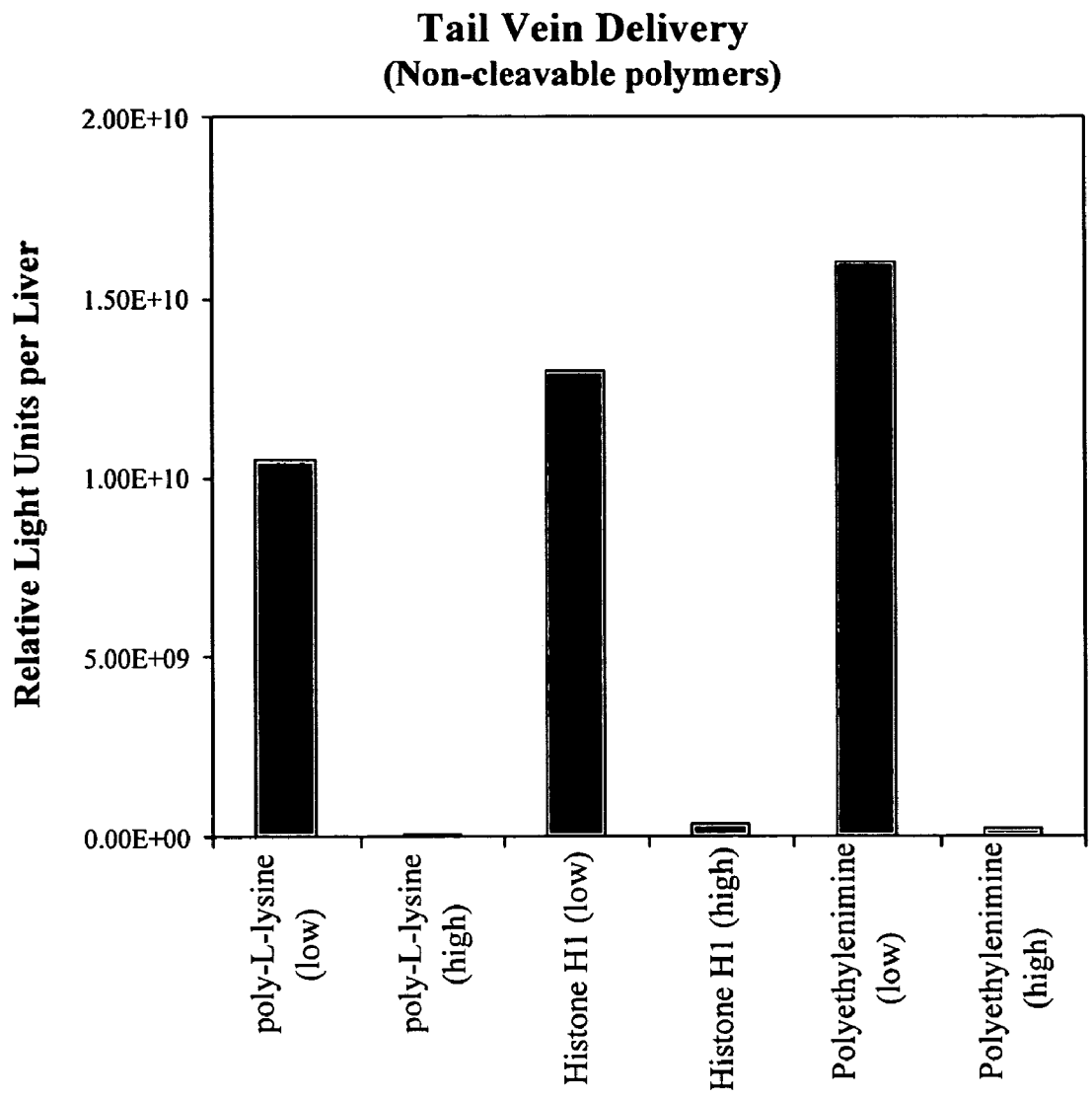
FIG. 4. Graph illustrating level of polynucleotide delivery following tail vein injection of pCILuc/polycation complexes in 2.5 ml ringers solution in 25 gram mice.

FIG. 4 illustrates tail vein injections of pCILuc/polycation complexes in 2.5 ml ringers solution into 25 gram mice (ICR, Harlan) as previously described (Zhang et al. Hum. Gen. Ther. 10:1735, 1999) Plasmid DNA encoding the luciferase gene was complexed with various polycations at two different concentrations. Complexes were prepared at polycation to DNA charge ratios of 0.5:1 (low) and 5:1 (high). This resulted in the formation of net negatively charged particles and net positively charged particles respectively. 24 hours after tail vein injection the livers were removed, cell extracts were prepared, and assayed for luciferase activity. Only complexes with a net negative overall charge displayed high gene expression following intravascular delivery.

Example 12

Delivery to Rat Skeletal Muscle cells In Vivo Using Intra-iliac Injection

A. Delivery of DNA and polycation/DNA to skeletal muscle via Iliac injection in Rat: Solutions were injected into iliac artery of rats using a Harvard Apparatus PHD 2000 programmable syringe pump. Specifically, animals were anesthetized and the surgical field shaved and prepped with an antiseptic. Harlan Sprague Dawley rats, approximately 150 g, were placed on a heating pad to prevent loss of body heat during the surgical procedure. A midline abdominal incision was made after which skin flaps were folded away and held with clamps to expose the target area. A moist gauze was applied to prevent excessive drying of internal organs. Intestines were moved to visualize the iliac veins and arteries. Microvessel clips were placed on the external iliac, caudal epigastric, internal iliac, deferent duct, and gluteal arteries and veins to block both outflow and inflow of the blood to the leg. An efflux enhancer solution (e.g., 0.5 mg papaverine in 3 ml saline) was pre-injected into the external iliac artery though a 25 g needle. Ten min later, 10 mL injection solution containing the indicated complexes was injected in approximately 10 seconds, unless otherwise indicated. The microvessel clips were removed 2 minutes after the injection and bleeding was controlled with pressure and gel foam. The abdominal muscles and skin were closed with 4-0 dexon suture. Seven days after injection, the animals were sacrificed, and a luciferase assays were conducted on leg muscles. Luciferase expression was determined as previously reported [Wolff et al. 1990].

A. 250 μg pCI-Luc plasmid DNA in 10 ml Ringer's injection solution was injected into iliac artery using varying injection rates. Results show that efficiency of delivery is affected by the rate of solution injection.

| | Injection Rate | | | |
|---|---|---|---|---|
| muscle | 0.83 ml/sec n = 2 | 0.56 ml/sec n = 4 | 0.42 ml/sec n = 3 | 0.33 ml/sec n = 3 |
| quad | 1109 ± 1183 | 384 ± 386 | 733 ± 154 | 221 ± 246 |
| biceps | 1476 ± 1138 | 276 ± 185 | 604 ± 122 | 83 ± 37 |
| hamstring | 2413 ± 1045 | 2071 ± 942 | 1635 ± 643 | 706 ± 384 |
| gastrocnemius | 1852 ± 1316 | 2274 ± 673 | 2088 ± 329 | 1078 ± 372 |
| shin | 774 ± 610 | 367 ± 361 | 289 ± 274 | 189 ± 63 |
| foot | 6 ± 5.5 | 8.9 ± 10.7 | 4.3 ± 2.2 | 0.9 ± 0.2 |
| total | 7397 ± 4456 | 7389 ± 2062 | 6664 ± 1001 | 3338 ± 1762 |

B. PEI/DNA and histone H1/DNA particles in 10 ml saline solution were injected into rat leg muscle by a single intra-arterial injection into the external iliac as described. Each rat received complexes containing 100 μg plasmid DNA. Results indicated delivery of the negatively charged complexes containing luciferase-expressing plasmid to muscles throughout the leg via injection into a afferent artery.

Luciferase expression in multiple muscles of the leg following injection of DNA/PEI or DNA/Histone HI particles.

| Muscle Group | Total RLUs | μg Luciferase |
|---|---|---|
| DNA/PEI particles (1:0.5 charge ratio) | | |
| muscle group 1 (upper leg anterior) | $3.50 \times 10^9$ | 0.180 |
| muscle group 2 (upper leg posterior) | $3.96 \times 10^9$ | 0.202 |
| muscle group 3 (upper leg medial) | $7.20 \times 10^9$ | 0.368 |
| muscle group 4 (lower leg posterior) | $9.90 \times 10^9$ | 0.505 |
| muscle group 5 (lower leg anterior) | $9.47 \times 10^8$ | 0.048 |
| muscle group 6 (foot) | $6.72 \times 10^6$ | 0.0003 |
| Total/leg | $25.51 \times 10^9$ | 1.303 |
| DNA/PEI particles (1:5 charge ratio) | | |
| muscle group 1 (upper leg anterior) | $1.77 \times 10^7$ | 0.0009 |
| muscle group 2 (upper leg posterior) | $1.47 \times 10^7$ | 0.0008 |
| muscle group 3 (upper leg medial) | $5.60 \times 10^6$ | 0.00003 |
| muscle group 4 (lower leg posterior) | $7.46 \times 10^6$ | 0.00004 |
| muscle group 5 (lower leg anterior) | $6.84 \times 10^6$ | 0.00003 |
| muscle group 6 (foot) | $1.55 \times 10^6$ | 0.000008 |
| Total/leg | $5.39 \times 10^7$ | 0.0018 |
| DNA/histone H1 particles (1:0.5 charge ratio) | | |
| muscle group 1 (upper leg anterior) | $3.12 \times 10^9$ | 0.180 |
| muscle group 2 (upper leg posterior) | $9.13 \times 10^9$ | 0.202 |
| muscle group 3 (upper leg medial) | $1.23 \times 10^{10}$ | 0.368 |
| muscle group 4 (lower leg posterior) | $5.73 \times 10^9$ | 0.505 |
| muscle group 5 (lower leg anterior) | $4.81 \times 10^8$ | 0.048 |
| muscle group 6 (foot) | $6.49 \times 10^6$ | 0.0003 |
| Total/leg | $3.08 \times 10^{10}$ | 1.57 |

-continued

| Muscle Group | Total RLUs | µg Luciferase |
|---|---|---|
| DNA/histone H1 particles (1:5 charge ratio) | | |
| muscle group 1 (upper leg anterior) | $1.42 \times 10^7$ | 0.0007 |
| muscle group 2 (upper leg posterior) | $5.94 \times 10^6$ | 0.0003 |
| muscle group 3 (upper leg medial) | $3.09 \times 10^6$ | 0.0002 |
| muscle group 4 (lower leg posterior) | $2.53 \times 10^6$ | 0.0001 |
| muscle group 5 (lower leg anterior) | $2.85 \times 10^6$ | 0.0001 |
| muscle group 6 (foot) | $1.84 \times 10^5$ | 0.000009 |
| Total/leg | $2.88 \times 10^7$ | 0.0014 |

C. Rat Iliac Injections of pDNA and pDNA/Polycation/Polyanion Complexes in Different Solutions: Solution A was normal saline. Solution B (low salt) was prepared consisting of 290 mM glucose (Sigma Chemical Company), 5 mM HEPES (Sigma Chemical Company), adjusted to pH 7.5.

Several complexes were prepared as follows:
Complex I. pDNA (250 µg, 125 µL of a 2 µg/µL solution in water) was added to 25 mL of Solution A.
Complex II. pDNA (250 µg, 125 µL of a 2 µg/µL solution in water) was added to 25 mL of Solution B.
Complex III. pDNA (250 µg, 125 µL of a 2 µg/µL solution in water) was added to 25 mL of Solution A. To this solution was added Poly-L-Lysine Hydrobromide (473 µg, 47.3 µL of a 10 mg/mL solution in water, Sigma), and the sample was mixed. To this solution was added Succinylated Poly-L-Lysine (1721 µg, 34.4 µL of a 50 mg/mL solution in water, Sigma), and the sample was mixed.
Complex IV. pDNA (250 µg, 125 µL of a 2 µg/µL solution in water) was added to 25 mL of Solution B. To this solution was added Poly-L-Lysine Hydrobromide (473 µg, 47.3 µL of a 10 mg/mL solution in water, Sigma), and the sample was mixed. To this solution was added Succinylated Poly-L-Lysine (1721 µg, 34.4 µL of a 50 mg/mL solution in water, Sigma), and the sample was mixed.

Rat iliac injections of 10 mL of solution (n=2) were conducted as previously described. Seven days after injection, the animal was sacrificed, and a luciferase assay was conducted on the leg muscles. The results indicate that naked plasmid is delivered and expressed in muscle following iliac injection in solution A and solution B. pDNA/Polycation/Polyanion complexes were delivered more efficiently with solution B than with solution A.

| Complex Number | Muscle Group | Tissue Volume | n1 | n2 |
|---|---|---|---|---|
| Complex I | Quadriceps | 15 mL | 12,514,072 | 16,227,067 |
| | Biceps | 15 mL | 9,586,089 | 19,093,910 |
| | Hamstring | 15 mL | 16,854,596 | 17,801,864 |
| | Gastrocnemius | 15 mL | 21,112,660 | 23,629,012 |
| | Lower shin | 5 mL | 6,996,074 | 4,859,628 |
| | Foot | 2 mL | 664,633 | 492,209 |
| Complex II | Quadriceps | 15 mL | 9,152,141 | 7,472,630 |
| | Biceps | 15 mL | 6,685,673 | 10,358,753 |
| | Hamstring | 15 mL | 13,285,607 | 10,120,048 |
| | Gastrocnemius | 15 mL | 15,893,838 | 15,643,649 |
| | Lower shin | 5 mL | 5,244,860 | 4,040,980 |
| | Foot | 2 mL | 1,053,676 | 1,805,209 |
| Complex III | Quadriceps | 15 mL | 13,681 | 4,519 |
| | Biceps | 15 mL | 5,910 | 2,344 |
| | Hamstring | 15 mL | 7,471 | 2,593 |
| | Gastrocnemius | 15 mL | 3,402 | 3,106 |
| | Lower shin | 5 mL | 3,605 | 3,602 |
| | Foot | 2 mL | 320 | 4,144 |

-continued

| Complex Number | Muscle Group | Tissue Volume | n1 | n2 |
|---|---|---|---|---|
| Complex IV | Quadriceps | 15 mL | 25,892 | 31,365 |
| | Biceps | 15 mL | 8,404 | 10,196 |
| | Hamstring | 15 mL | 14,034 | 15,501 |
| | Gastrocnemius | 15 mL | 9,545 | 22,867 |
| | Lower shin | 5 mL | 24,146 | 10,229 |
| | Foot | 2 mL | 16,121 | 19,215 |

D. Expression of a therapeutic gene in skeletal muscle tissue: 500 µg plasmid DNA (pCI-hF9) expressing the human factor IX gene (cDNA) under transcriptional control of the human cytomegalovirus promoter in 10 ml Ringer's was delivered to rat hind limb skeletal muscle as described above. The rats were immunosuppressed by treatment with 10 mg/kg of FK506 orally and 1 mg/kg dexamethasone subcutaneously one day prior to, one hour prior to, and one day after plasmid DNA delivery The rats were sacrificed after 3 weeks, at which time the hind limb skeletal muscles were removed and homogenized in a total volume of 60 ml. Human factor IX levels in the rat sera were determined using an ELISA and compared to normal human serum. Expression levels in 3 rats were 1400, 1000, and 1150 ng/ml extract, respectively. Therefore, the total amount of human factor IX present in the rat muscle tissue three weeks after pDNA delivery was approximately 70 µg.

E. Expression of secreted alkaline phosphate from rat skeletal muscle cells: A plasmid DNA expression vector (pMIR54) was constructed in which the secreted alkaline phosphatase (SEAP) gene (obtained from plasmid pSEAP-2 basic, Clontech) is under transcriptional control of the human cytomegalovirus promoter. A solution of 500 µg pMIR54 in 10 ml Ringer's was injected into the iliac artery of rats as described. The rats were immunosuppressed as described above. In addition, rats were treated with 2.5 mg/kg FK506 daily. Blood samples were obtained from the rats at several time. SEAP expression was determined using a chemiluminescent assay (Tropix) and compared to a standard curve.

| | SEAP expression (ng SEAP per ml serum) | |
|---|---|---|
| | Day 7 | Day 14 |
| Rat 2889 | 2,301 | 1,407 |
| Rat 2992 | 3,735 | 2,942 |

Example 13

Expression in Multiple Muscle Groups

500 µg of pCI-Luc in 10 ml of normal saline solution was injected into the femoral artery of adult rats in which a tourniquet was applied to the outside of the leg proximal (tourniquet was applied to the upper portion of the quadriceps group of muscles) to the injection site. Five days after injection, the different muscle groups from the leg were removed and cut into equal sections. Each section was placed into lysis buffer, the muscles were homogenized and 10 µl of the resulting lysates were assayed for luciferase activity. High levels of luciferase expression were expressed in all muscle groups that were located distal to the tourniquet. These included the biceps femoris, posterior muscles of the upper leg, gastrocnemius, muscles of the lower leg, and muscles of the plantar surface. Intravascularly-administered plasmid DNA is expressed efficiently in multiple muscle groups when blood flow is impeded using an external tourniquet. This result indicates that applying a tourniquet to occlude fluid flow from the limb during injection can substitute for clamping of individual vessels and is less invasive.

| Muscle Group | Total Luciferase (ng/muscle group) | |
|---|---|---|
| | without tourniquet | with tourniquet |
| Upper leg anterior (quadriceps) | 0.010 | 0.181* |
| Upper leg middle (biceps femoris) | 0.011 | 28.3 |
| Upper leg posterior (hamstrings) | 2.16 | 146 |
| Lower leg posterior (gastrocnemius) | 1.57 | 253.6 |
| Lower leg anterior (lower shin muscles) | 0.72 | 115.2 |
| Muscles of the plantar surface | 0.202 | 0.433 |

*majority of this muscle group was above the tourniquet

Example 14

Labeled pDNA Distribution in Muscle

Figure 5:
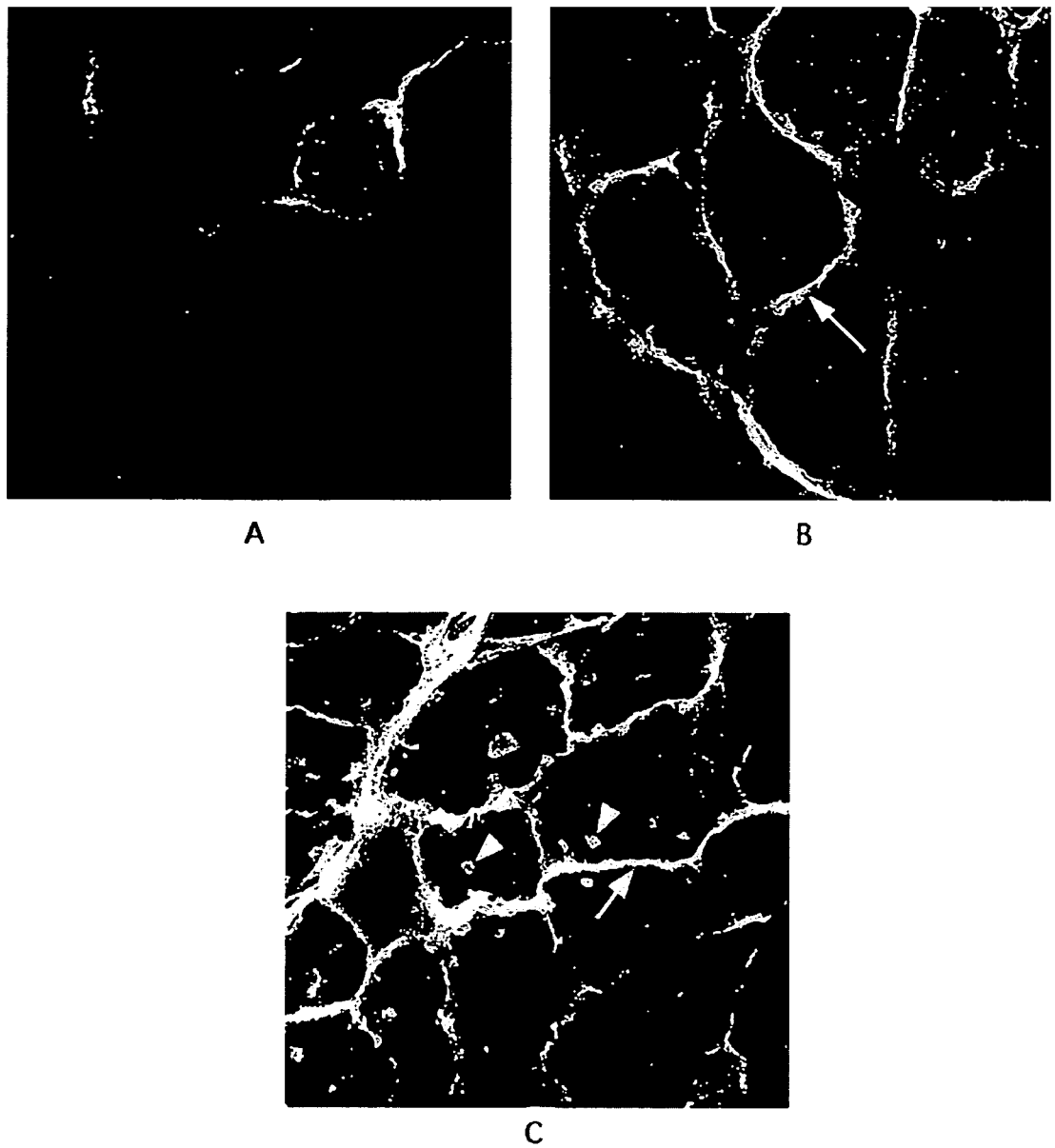
FIG. 5A-5C. Muscle sections obtained 5 min (A and B) and 1 h (C) after 50 μg of Rh-pDNA in 10 ml of normal saline were injected within 7 sec into the femoral artery of rat without impeding the outflow (A) or impeding outflow (B and C). Arrows indicate Rh-pDNA between cells and arrowheads indicate pDNA inside myofibers. Magnification: ×1260.

Rhodamine-labeled pDNA (Rh-pDNA) was injected into the femoral artery of rats under various conditions in order to explore the uptake mechanism in muscle as was done for liver. When the injections were performed without impeding blood outflow (low intravascular pressure), almost no DNA was detected within the muscle tissues or vessels. FIG. 5A presents a rare field when some DNA can be seen between muscle cells. When the injections were performed with outflow occlusion (increased intravascular pressure), Rh-pDNA was detected throughout all the muscle (FIGS. 5B and C). At 5 min after injection, examination of tissue sections indicated that the majority of the Rh-pDNA was surrounding the muscle cells and there was no intracellular staining (FIG. 5B, arrow). At one hour after injection, substantial amounts of DNA can be seen inside the cells (FIG. 5C, arrowhead). Examination of serial confocal sections indicates that the intracellular staining pattern is punctate, unlikely consistent with a T tubular distribution.

Example 15

Intra-Arterial Delivery of Polynucleotides to Limb Skeletal Muscles in Normal and Dystrophic Dog Juvenile male Golden Retriever dogs of 3 to 12 kg body weight underwent intra-arterial injections in their limbs following anesthesia. Anesthesia was with intravascular injection of propofol followed by isoflurane inhalant. For forearm injections, the arm was put at the extension and external rotation position and a 3 cm incision was made at the conjunction of armpit and upper arm and near the inside edge of the brachial biceps. After separating the brachial artery from the brachial vein and median nerve, a catheter (3-4F) was inserted anterograde into the brachial artery until the tip of the catheter reached to the elbow and was fixed by ligation. In some cases the brachial vein was clamped. Blood circulation of the forelimb was further inhibited by using a tourniquet placed around the upper limb up to the elbow (10 minutes maximum). For whole hindleg injections, an incision was made through the midline of the abdomen one inch below the umbilicus to the pubis. Connective tissue was separated to expose the common iliac artery and vein, external iliac artery and vein, internal iliac artery and vein, inferior epigastric artery and vein, superficial epigastric artery and vein, and the superficial iliac circumflex artery and vein. Clamps were placed on the inferior epigastric artery and vein, superficial epigastric artery and vein, and the superficial iliac circumflex artery and vein. An catheter (F5) was placed into the distal part of the iliac artery to the femoral artery and secured by ligation at the beginning of the femoral artery. Clamps are then placed on the external iliac vein, internal iliac artery and vein, and the common iliac artery and vein.

A 17% papaverine/saline solution was injected to increase vessel dilation (10-50 ml depending on animal size). After 5 minutes a plasmid DNA/saline solution was injected using a nitrogen-pressurized cylinder set at 65 psi. For the forelimbs, the injection volume was 50-200 ml. For whole leg injections, the injection volume was 60-500 ml. Injection rates varied from 20 s to 120 s. Two min after injection, the clamps and tourniquet were released and the catheters were removed.

Figure 6:
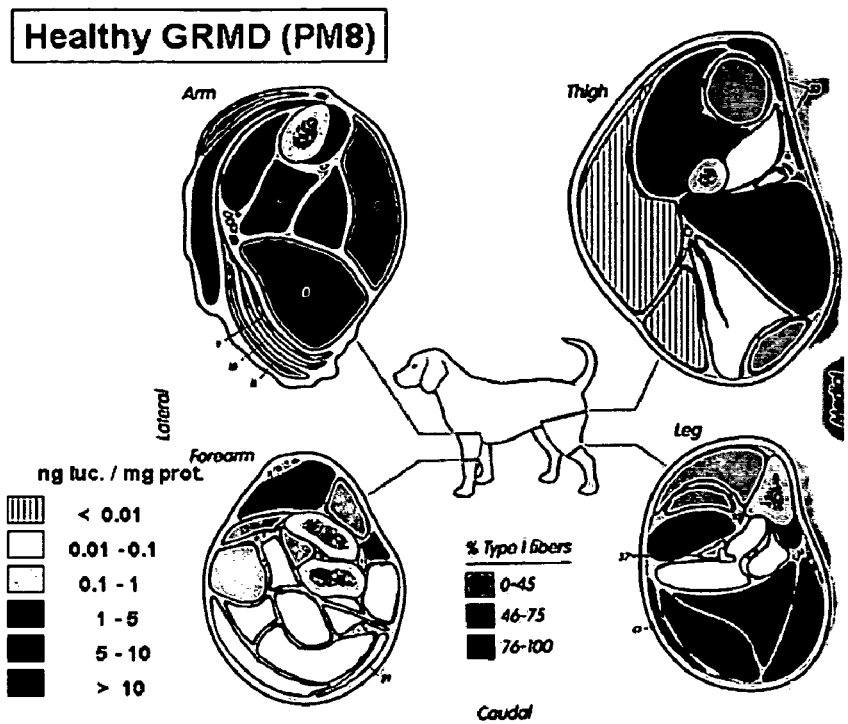
FIG. 6. Illustration of luciferase expression in leg muscles of dystrophic and normal dog after intra-arterial injection of pCI-Luc plasmid under elevated pressure. Panel A shows expression distribution in normal dog. Panel B shows expression distribution in dystrophic dog model.
Figure 6:
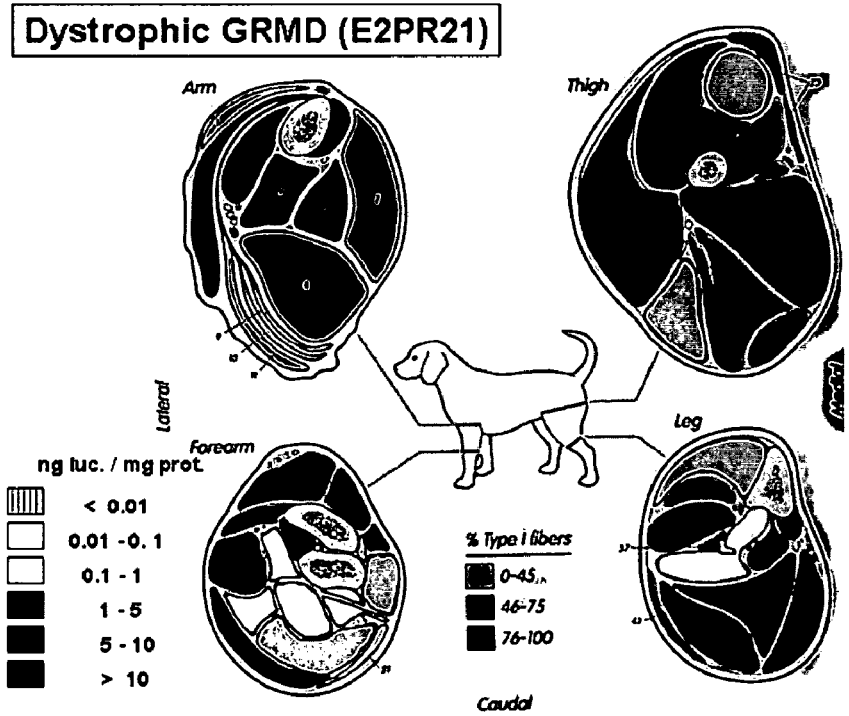

One forelimb and the opposite hindlimb or all four limbs were injected on day one with pMI-Luc+ (20-50 mg) or the dystrophin plasmid (50-330 mg). In these vectors, the reporter genes are under transcriptional control of the muscle creatine kinase promoter, which has been shown to direct sustained, high level expression in muscle. The animals were sacrificed at 7 days and all muscles were analyzed for gene expression. Uninjected limbs or limbs injected with saline were used to test for revertants. Results are shown below and graphically summarized in FIG. 6. FIG. 6A illustrates the distribution of luciferase expression in normal dog. FIG. 6B illustrates the distribution of luciferase expression in the dystrophic dog model.

Luciferase expression after of delivery pCI-Luc polynucleotide in dog skeletal muscle cells. Numbers given in pg Luciferase per mg total protein.

| | | | GRMD dog | | healthy dog | |
|---|---|---|---|---|---|---|
| | | | left | right | left | right |
| | antebrachial muscles | | | | | |
| dorsolateral | extensor carpi radialis | | | | 0.8 | 633 |
| | extensor digitorium communis | | 5 | 1570 | | 299 |
| | extensor digitorium lateralis | | | 7915 | | 438.5 |
| | extensor carpi ulnaris | | | 671 | | 21.5 |
| | extensor pollicis longus et indicis proprius | | | 6763 | | 2456.7 |
| | abductor pollicis longus | | | 16724 | | 292.4 |
| | supinator | | 9 | 14395 | 3.3 | 1920.8 |

-continued

|  |  | GRMD dog | | healthy dog | |
|---|---|---|---|---|---|
|  |  | left | right | left | right |
| caudal | flexor carpi radialis | 3 | 828 | 1.5 | 116.2 |
|  | flexor carpi ulnaris |  | 270 |  | 6.1 |
|  | flexor digitorum superficialis |  | 2017 |  | 43.5 |
|  | flexor digitorum profundus |  | 49 |  | 11.3 |
|  | pronator teres |  | 9231 | 5.2 | 270.6 |
| forepaw | forepaw | 10 | 958 | 2 | 1048.7 |
| other | brachi radialis |  |  |  | 545.1 |
| muscles of the crus | | | | | |
| craniolateral | tibialis cranialis | 980 | 1.4 | 1.7 |  |
|  | extensor digitorum longus | 992 | 0.3 |  |  |
|  | peroneus longus | 4116 | 0.3 | 127.8 |  |
|  | peroneus brevis |  |  | 6.2 |  |
|  | extensor digitorum lateralis |  | 0.2 |  |  |
| caudal | gastrocnemius | 4365 | 0.1 | 3 | 0.1 |
|  | flexor digitorum profundus | 1912 | 1.9 | 3 |  |
|  | tibialis caudalis |  | 0.4 |  |  |
|  | popliteus | 9821 | 0.3 |  |  |
| other | Testes | 0.1 |  |  |  |
|  | Liver #1 |  | 0.3 |  |  |
| muscles of the pelvic limb | | | | | |
| thigh | gluteus superficialis |  | 1.4 | 4.9 |  |
|  | gluteus medius | 4 | 0.2 | 0.1 |  |
|  | sartorius |  |  | 661.2 |  |
|  | tensor fasciae latae |  | 0.5 | 369.7 |  |
|  | biceps femoris | 10312 | 1.1 | 0.1 |  |
|  |  |  |  | 0.6 |  |
|  | semimembranosus | 5988 | 1.7 | 49.8 |  |
|  | semitendinosus | 432 | 1.1 | 0.1 |  |
|  | abductor magnus brevis | 4103 | 2 | 3644.8 |  |
|  | sartorius cranial part | 4664 | 0.9 |  |  |
|  | rectus femoris | 396 | 0.1 | 179.9 |  |
|  | vastus medialis | 2588 | 0.5 | 7.4 |  |
|  | vastus intermedius | 4469 | 3.2 | 12448.7 |  |
|  | vastus lateralis | 2102 | 1 | 2927.8 |  |
|  | pectineus | 737 | 0.1 | 11.9 |  |
|  | gracilis | 1826 | 0.5 | 146 |  |
| gluteal region | piriformis |  | 14 | 1.2 |  |
| and | gemellus |  |  | 3 |  |
| hip joint | quadratus femoris | 911 | 0.1 | 1 |  |
|  | gluteus profundus |  | 0 | 1.8 |  |
|  | obturator externus |  |  | 1.8 |  |
|  | biceps brachialis |  |  |  | 0.1 |

Example 16

Intraarterial Injections in Monkeys

Seven Rhesus macaque monkeys (5 males; 2 females, 6-20 yrs old) of 6 to 13.7 kg body weight underwent intraarterial injections in their limbs following anesthesia with ketamine and halothane. For the forearm injections, a longitudinal incision, ~3 cm in length, was made on the skin along the inside edge of the biceps brachii and 2 cm above the elbow. After separating the artery from surrounding tissues and veins, a 20 g catheter was inserted into the brachial artery anterogradely and ligated in place. For the lower leg injections, the procedure was essentially the same as that used in the arm, but the incision was located on the upper edge of the popliteal fossae and the 20 g catheter was inserted into the popliteal artery. For both the arm and leg injections, blood flow was impeded by a sphygmomanometer cuff surrounding the arm or leg proximal to the injection site. After the sphygmomanometer was inflated to more than 300 mmHg air pressure, the catheterized vessels were injected with 30 ml of normal saline containing 5 mg papaverine (Sigma Co.). Five min. later, a saline solution containing 100 µg pDNA/ml solution was rapidly injected within 30 to 45 sec. For the arms, the volume of each injection was 75 ml and 90 ml in the first two animals and 120 ml thereafter. The injection volume was about 180 ml for the lower legs. The DNA solutions were injected using a nitrogen-pressurized cylinder. Two min after injection, the catheters were removed and the sphygmomanometer deflated.

Four monkeys received injections in one arm and one leg with muscle biopsies taken at one (#1-3) or two weeks (#4). Three monkeys (#5-7) received injections in all four limbs (one arm and leg on day 1 and the other arm and leg on day 3) with muscle biopsies taken at one week. In monkeys #6 and #7, one arm and one leg were injected with pCI-LacZ (LacZ expression driven by the CMV immediate-early promoter; pCI from Promega, Madison, Wis.). All other injections were with pCI-Luc$^+$ (Luciferase expression driven by the CMV immediate-early promoter). Monkeys were sacrificed at 14 to 16 days after injection and target muscles of their limbs were assessed for either luciferase or β-galactosidase expression.

All seven monkeys tolerated the procedure well and had full function of their arms, hands, legs and feet following the procedure. In particular, this indicates lack of damage to the radial nerve, which could have been sensitive to the inflated sphygmomanometer surrounding the upper arm. Swelling in the target limbs, a putative correlate of successful gene transfer, was noted afterwards but completely subsided by the next day. When the monkeys awakened from the anesthesia 15 to 30 min after the procedure, they did not appear to be in any discomfort beyond that of normal surgical recovery. Occasionally, the skin in the target limb had some spots of hemorrhage that resolved within several days.

For the β-galactosidase assays, muscle samples were taken from the proximal, middle, and distal positions of each muscle, cut into small pieces, frozen in cold isopentane, and stored at −80° C. Samples were randomly chosen from each muscle sample (for every position) and 10 μm-thick cryostat sections were made. Every tenth section, for a total of 20 sections, was stained and analyzed. The sections were incubated in X-gal staining solution (5 mM potassium ferricyanide, 5 mM potassium ferrocyanide, 1 mM magnesium chloride, 1 mM X-gal in 0.1 M PBS, pH 7.6) for 4-8 hours at room temperature and counterstained with hematoxylin and eosin. Three sections were selected randomly from the 20 sections of each position (usually the 4th, 11th and 17th sections, but an adjacent section was used if these sections were not intact). The number of β-galactosidase-positive and total cells were determined within a cross area in each section by moving the counter grid from the top edge of the section to the bottom and from the left edge to the right. The percentage of β-galactosidase-positive cells for each muscle was determined from the result of positive number divided by total cell number. A weighted average for the percent of transfected cells for each extremity muscle was determined as follows: $(\Sigma Ai*Mi)/M$ where Ai is percent of transfected cells for one muscle, Mi—weight of that muscle and M—whole weight of all muscles.

For luciferase expression, relative light units (RLU) were converted to nanograms of luciferase using a luciferase standard curve in which luciferase protein $(pg) = RLU \times 5.1 \times 10^{-5}$.

Figure 7:
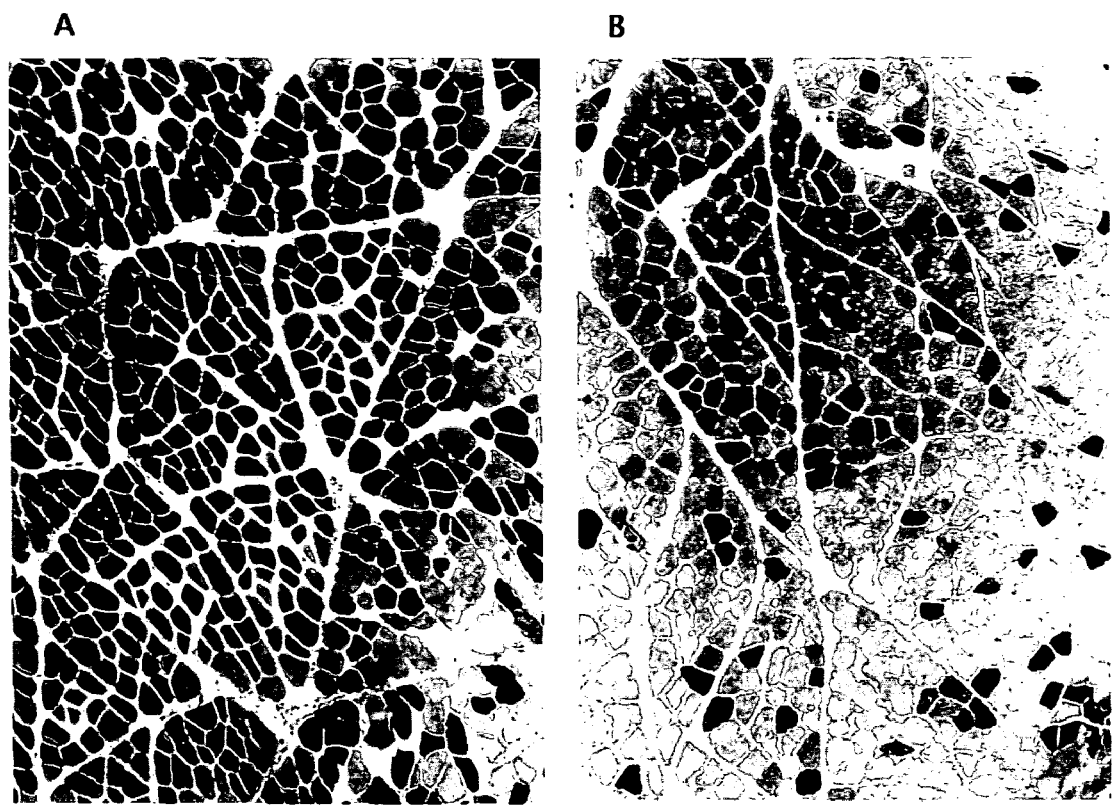
FIG. 7A-7B. Photomicrographs of muscle sections histochemically stained for β-galactosidase expression. Panel A represents a muscle (pronator teres) with a high level of expression; panel B represents a muscle (abductor pollicis longus) with an average level of expression. Magnification: ×160.

After intraarterial injection of pCI-LacZ DNA, β-galactosidase expression was found in myofibers. Large numbers of β-galactosidase-positive myofibers were found in both leg and arm muscles, ranging from less than 1% to more than 30% in different muscles (below and FIG. 7). The average percentage for all four limbs injected was 7.4%, ranging from 6.3% to 9.9% for each of the limbs. The β-galactosidase percentages for specific muscle groups positively correlated with the luciferase levels in the same muscles (r=0.79). These results indicate that the intra-arterial injection of pCI-Luc$^+$ DNA yielded levels of luciferase expression in all muscles of forearm, hand, lower leg and foot, ranging from 345 to 7332 ng/g muscle. The variability in luciferase expression in arm muscles for different animals appears dependent upon whether the tip of the catheter was positioned in the radial or ulnar artery. The average luciferase expression levels in the limb muscles were 991.5±187 ng/g for the arm and 1186±673 ng/g for the leg.

A. Arm muscles

| Muscle group | | Muscle name | β-galactosidase (% positive) (n = 2) | Luciferase (ng/g muscle) (n = 5) |
|---|---|---|---|---|
| Anterior group | Superficial group | palmaris longus | 5.9 ± 0.9 | 2368 ± 1309 |
| | | pronator teres | 19.9 ± 9.4 | 1818 ± 336 |
| | | flexor carpi radialis | 7.8 ± 0.7 | 1885 ± 762 |
| | | flexor carpi ulnaris | 3.8 ± 3.0 | 852 ± 314 |
| | | flexor digitorum superficialis | 7.7 ± 1.2 | 1009 ± 189 |
| | Deep group | flexor digitorum profundis | 1.0 ± 0.5 | 544 ± 360 |
| | | pronator quadratus | 14.3 ± 11.1 | 1884 ± 331 |
| Posterior group | Superficial group | brachioradialis | 9.0 ± 8.7 | 1148 ± 942 |
| | | extensor carpi radialis longus | 6.6 ± 6.3 | 1179 ± 584 |
| | | extensor carpi radialis brevis | 9.4 ± 4.5 | 1118 ± 325 |
| | | extensor digitorum | 6.2 ± 5.4 | 1184 ± 94 |
| | | anconeus | 2.0 ± 0.3 | 1744 ± 372 |
| | | extensor carpi ulnaris | 0.6 ± 0.4 | 371 ± 86 |
| | | extensor pollicis longus | 6.9 ± 4.3 | 927 ± 228 |
| | Deep group | supinator | 15.1 ± 9.3 | 2398 ± 748 |
| | | abductor pollicis longus | 6.2 ± 3.8 | 927 ± 228 |
| | | extensor digiti secund et teriti | 6.0 ± 5.5 | 642 ± 168 |
| | | extensor digiti quart et minimi | 4.0 ± 3.5 | 593 ± 140 |
| Muscles of hand | | muscle of thumb | 15.7 ± 0.5 | 904 ± 494 |
| | | interosseus | 17.3 ± 4.3 | 1974 ± 185 |
| | | Weighted Average | 6.3 ± 0.04 | 991 ± 187 |

B. Leg muscles

| Muscle group | | Muscle name | β-galactosidase (%) (n = 2) | Luciferase (ng/g muscle) (n = 2) |
|---|---|---|---|---|
| Posterior group | Superficial group | gastrocnemius | 3.0 ± 2.5 | 743 ± 33 |
| | | soleus | 21.2 ± 1.4 | 2888 ± 2151 |
| | Deep group | popliteus | 37.1 ± 0.5 | 4423 ± 2657 |
| | | flexor digitorum longus | 8.9 ± 2.4 | 3504 ± 2151 |
| | | flexor hallucis longus | 9.7 ± 2.4 | 1355 ± 1224 |
| | | tibialis posterior | 28.7 ± 4.3 | 7332 ± 5117 |
| Anterior group | | tibialis anterior | 2.8 ± 0.2 | 716 ± 162 |
| | | extensor hallucis longus | 4.2 ± 1.4 | 810 ± 497 |
| | | extensor digitorum longus | 10.9 ± 1.0 | 3187 ± 1166 |
| | | abductor hallucis longus | 2.2 ± 0.2 | 345 ± 104 |

| | | | |
|---|---|---|---|
| Internal group | peronaus longus | 6.3 ± 2.5 | 626 ± 383 |
| | peronaus brevis | 8.9 ± 1.3 | 1300 ± 23 |
| Muscles of foot | extensor digitorum brevis | 6.2 ± 5.0 | 672 ± 607 |
| | extensor hallucis brevis | 2.4 ± 1.8 | 672 ± 607 |
| LEG MUSCLES Weighted Average | | 7.3 ± 0.1 | 1692 ± 768 |

Example 17

Increased Vascularization Following Delivery of a Therapeutic Polynucleotide to Primate Limb DNA delivery was performed via brachial artery with blood flow blocked by a sphygmomanometer cuff proximately to the injection site. Left arm was transfected with VEGF, while right arm was transfected with EPO. The Sartorious muscle from left leg was used as non-injected control. A male Rhesus monkey weighing 14 kg was used for these injections. The animal was anesthetized with Ketamine (10-15 mg/kg). A modified pediatric blood pressure cuff was positioned on the upper arm. The brachial artery was cannulated with a 4 F angiography catheter. The catheter was advanced so that the tip was positioned just below (distal) the blood pressure cuff. Prior to the injection, the blood pressure cuff was inflated so that the cuff pressure was at least 20 mmHg higher than the systolic blood pressure. After cuff inflation, papaverine (5 mg in 30 ml of saline) was injected by hand (~8 to 10 seconds). After 5 min, the pDNA solution was delivered rapidly with a high volume injection system. For the EPO injection, 10 mg of pDNA was added to 170 ml of saline and injected at a rate of 6.8 ml per second. For the VEGF injection, 10 mg of pDNA was added to 150 ml of saline, and injected at a rate of 5.4 ml per second.

After 65 days, the animal was euthanized by overdose I.V. injection of pentobarbital Ketamine (10 mg/kg). The entire Pronator quadratus and Pronator teres muscles from both sides were immediately harvested and fixed for 3 day in 10% neutral buffered formalin (VWR, Cleveland, Ohio). After fixation, an identical grossing was performed for left and right muscles and slices across the longitudinal muscles were taken. Specimens were routinely processed and embedded into paraffin (Sherwood Medical, St. Louis, Mo.). Four microns sections were mounted onto precleaned slides, and stained with hematoxylin and eosin (Surgipath, Richmond, Ill.) for pathological evaluation. Sections were examined under Axioplan-2 microscope and pictures were taken with the aid of AxioCam digital camera (both from Carl Zeiss, Goettingen, Germany).

To evaluate the effect of VEGF plasmid delivery on cell composition in muscle tissue and neo-angiogenesis, we used monoclonal mouse anti-human CD31 antibody (DAKO Corporation, Carpinteria Calif.). The immunostaining was performed using a standard protocol for paraffin sections. Briefly: four microns paraffin sections were deparaffinized and re-hydrated. Antigen retrieval was performed with DAKO Target Retrieval Solution (DAKO Corporation, Carpinteria Calif.) for 20 min at 97° C. To reduce non-specific binding the section were incubated in PBS containing 1% (wt/vol) BSA for 20 min at RT. Primary antibody 1:30 in PBS/BSA were applied for 30 min at RT. CD31 antibody were visualized with donkey anti-mouse Cy3-conjugated IgG, 1:400 (Jackson Immunoresearch Lab, West Grove Pa.) for 1 h at RT. ToPro-3 (Molecular Probes Inc.) was used for nuclei staining; 1:70,000 dilution incubated for 15 min at RT. Sections were mounted with Vectashield non-fluorescent mounting medium and examined under confocal Zeiss LSM 510 microscope (Carl Zeiss, Goettingen, Germany). Images were collected randomly under 400× magnification, each image representing 0.106 sq mm. Because muscle fibers and red blood cells have an autofluorescence in FITC channel we use 488 nm laser to visualize these structures. Morphometry analysis. Coded mages were opened in Adobe Photoshop 5.5 having image size 7×7 inches in 1×7 inches window, and a grid with rulers was overlaid. The number of muscle fibers, CD31 positive cells and total nuclei was counted in all 7 image's strips consecutively, without any knowledge of experimental design. T-Test for Two-Sample Unequal Variances was used for statistical analysis.

Figure 8:
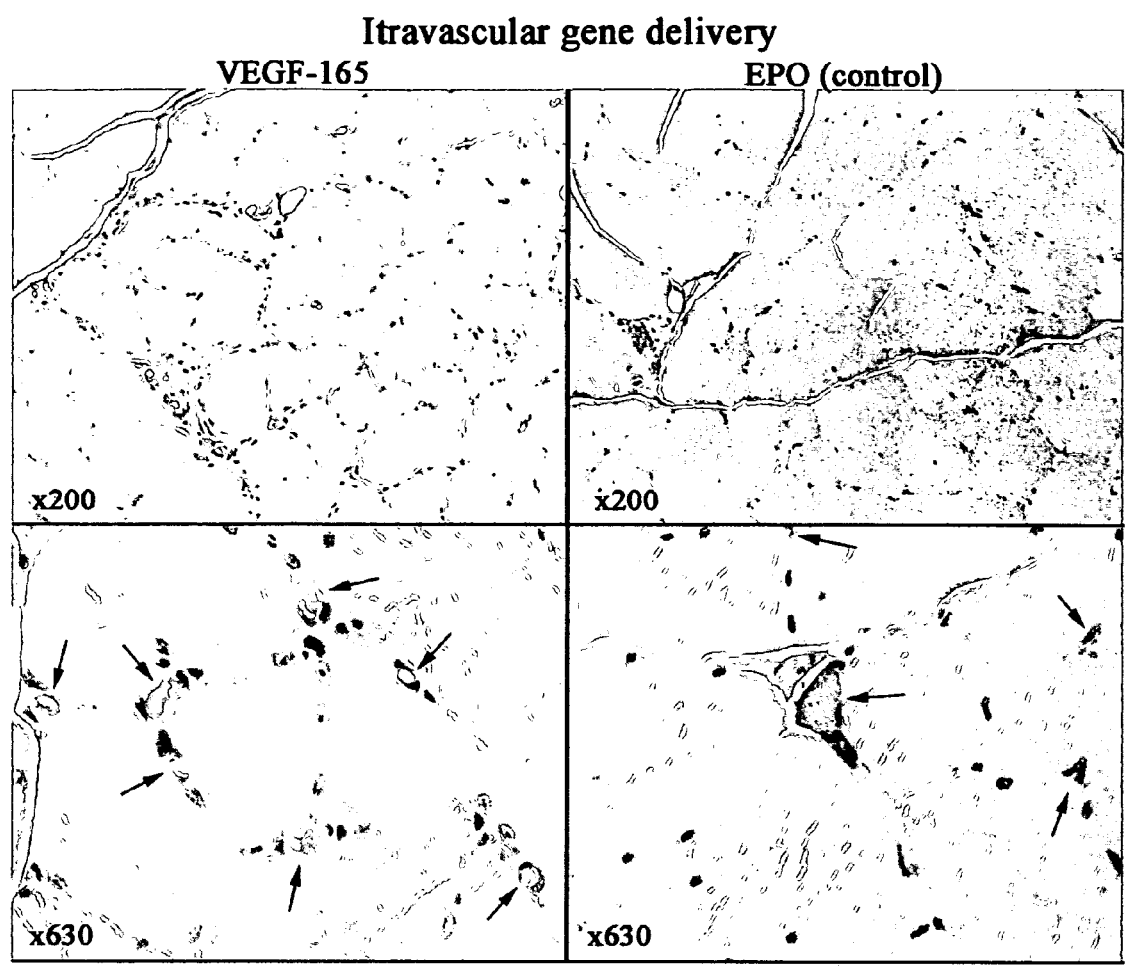
FIG. 8. Paraffin cross sections of the Pronator quadratus muscles stained with hematoxylin and eosin and examined under light microscope. Left panel—Pronator quadratus muscle transfected with VEGF-165 plasmid. Right panel—Pronator quadratus muscle transfected with EPO plasmid. Top left picture (VEGF-165) demonstrates increased number of vessels and interstitial cells (presumably—endothelial cells), as compared to right picture (EPO-control), magnification ×200. Bottom left picture (VEGF-165) demonstrates increased number of vessels, most small arteries and capillaries, as compare to right picture (EPO-control). Arrows indicate obvious vascular structures, magnification ×6300.
Figure 9:
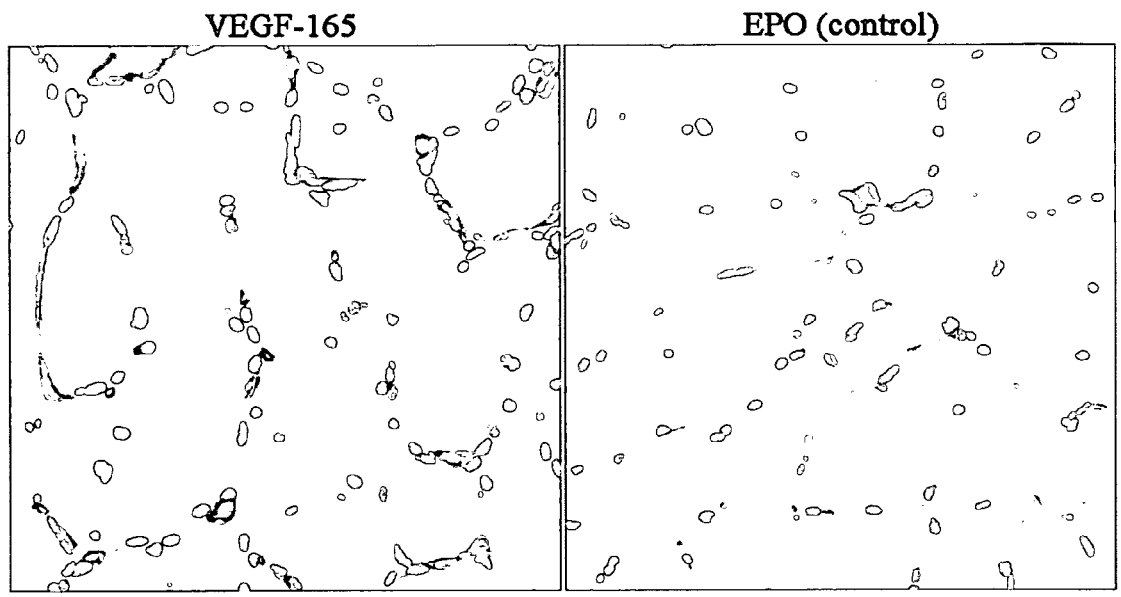
FIG. 9. Paraffin cross sections of the Pronator quadratus muscles immunostained for endothelial cell marker—CD31, and examined under confocal laser scanning microscope LSM 510, magnification ×400. CD31 marker visualized with Cy3 (black), nuclei with nucleic acid stains To Pro-3. Muscle fibers and red blood cells were visualized by 488 nm laser having autofluorescent emission. Left picture—Pronator quadratus muscle transfected with VEGF-165 plasmid, demonstrates increased of endothelial cells and small vessels, as compare to right picture (EPO-control). The number of CD31 positive cells was increased significantly in VEGF-165 transfected muscle by 61.7% (p<0.001).

Results: Microscopic evaluation did not reveal any notable pathology in either muscle regardless of the gene delivered. Also, neither muscle showed any notable presence of inflammatory cells, except for a few macrophages. Necrosis of single muscle fibers was extremely rare in both, occupying negligible volume and was not associated with infiltration/ vascularization. However, in muscles transfected with VEGF-165 plasmid, the interstitial cell and vascular density (observed in H&E-stained slides) was obviously increased (FIG. 8), as compare to EPO plasmid administered muscle (FIG. 8). Based on morphologic evaluation, these newly arrived interstitial cells we suggested to be endothelial and adventitial cells, smooth muscle cells, and fibroblasts. To evaluate participation of endothelial cells in this neo-morphogenesis, we have counted the number of CD31 positive cells in EPO and VEGF delivered Pronator quadratus muscles (FIG. 9). To assure that comparable specimens were analyzed in right and left muscles, the number of muscle fibers was counted per area unit (0.106 sq mm). The VEGF and EPO administered muscles were not different in muscle fiber number (means 30.5 and 31.6). The number of CD31 positive cells however was significantly increased by 61.7% p<0.001 (means 53.2 vs 32.9).

Example 18

Intravenous Injection Provides Effective Delivery of Polynucleotides to Limb Parenchymal Cells A. Injection into the small (external) saphenous vein: 120-140 g adult Sprague-Dawley rats were anesthetized with 80 mg/kg ketamine and 40 mg/kg xylazine and the surgical field was shaved and prepped with an antiseptic. The animals were placed on a heating pad to prevent loss of body heat during the surgical procedure. A 4 cm long abdominal midline incision was made after which skin flaps were folded away and held with clamps to expose the target area. A moist gauze was applied to prevent excessive drying of internal organs. Intestines were moved to visualize the iliac veins and arteries. Microvessel clips were placed on the external iliac, caudal epigastric, internal iliac, deferent duct, and gluteal arteries and veins as well as on the inferior vena cava near the bifurcation to block both outflow and inflow of the blood to the leg. An efflux enhancer solution (e.g., 0.5 mg papaverine in 3 ml saline) was injected into the small saphenous vein though a 27 g needle. 1-10 minutes later, a 27 G butterfly needle was inserted into the same site and 10.5 ml normal saline containing 500 μg pMIR48 plasmid DNA encoding firefly Luciferase was injected at a rate of 0.583 ml/sec. Fluid was injected in the direction of normal blood flow. The microvessel clips were removed 2 minutes after the injection and bleeding was controlled with pressure and gel foam. The abdominal muscles and skin were closed with 4-0 dexon suture. Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per gram of muscle tissue was determined. The muscle descriptions indicate the following muscle groups of the hindlimb: Quad—anterior muscles of upper leg; Biceps—medial muscles of upper leg; Hamstring—posterior muscles of upper leg; Gastroc—posterior muscles of lower leg; Shin—anterior muscles of lower leg; Foot—muscles of the dorsal foot. Luciferase expression was observed in muscles throughout the limb distal to the occlusion. Highest expression levels were observed near the site of injection.

Gene delivery to muscles of the leg by intravenous injection of plasmid DNA.

| | ng Luciferase/g Muscle | | | | | | |
|---|---|---|---|---|---|---|---|
| animal | Quad | Biceps | Hamstring | Gastroc | Shin | Foot | total |
| 1 | 664.8 | 402.8 | 98.0 | 237.0 | 359.2 | 0.6 | 360.8 |
| 2 | 1690.1 | 1515.8 | 848.7 | 195.7 | 3471.4 | 4.6 | 1200.4 |
| 3 | 619.5 | 353.3 | 45.5 | 104.6 | 61.8 | 0.3 | 260.0 |
| mean | 991.5 | 757.3 | 330.7 | 179.1 | 1297.5 | 1.8 | 607.1 |
| SEM | 349.6 | 379.5 | 259.4 | 39.1 | 1090.4 | 1.4 | 298.1 |

B. Injection into Medial saphenous vein: In a similar experiment, a 10 ml solution containing 500 μg plasmid DNA (pMIR48) was injected (antegrade direction) into the medial saphenous vein at a flow rate of 20 ml/min.

Gene delivery to muscles of the leg by intravenous injection of plasmid DNA.

After 2 minutes the clamps were removed and the vein allowed to reperfuse. Within several minutes the muscle regained a pink color and the vein returned to normal. Luciferase expression was determined as above. Luciferase expression was observed in muscles throughout the limb distal to the occlusion.

Gene delivery to muscles of the leg by intravenous injection of plasmid DNA.

| | ng Luciferase/g Muscle | | | | | | |
|---|---|---|---|---|---|---|---|
| animal | Quad | Biceps | Hamstring | Gastroc | Shin | Foot | total |
| 1 | 5.5 | 8.0 | 396.0 | 474.0 | 180.3 | 0.5 | 190.0 |
| 2 | 7.7 | 7.9 | 201.0 | 430.4 | 100.3 | 1.0 | 143.4 |
| 3 | 1.3 | 3.0 | 54.5 | 521.0 | 119.4 | 0.3 | 118.7 |
| mean | 4.8 | 6.3 | 217.1 | 475.1 | 133.4 | 0.6 | 150.7 |
| SEM | 1.9 | 1.6 | 98.9 | 26.1 | 24.1 | 0.2 | 20.9 |

Example 19

Intravenous Delivery of Polynucleotides to Limb Parenchymal Cells Using a Cuff to Occlude Blood Flow to and from the Limb 500 μg of pDNA (pCI-Luc-K) in 3 ml of normal saline solution (NSS) was used for all intravascular and intramuscular DNA injections into ~150 g Sprague-Dawley rats (Harlan Laboratories, Indianapolis, Ind.). Blood flow to and from the limb was restricted just prior to and during the injection, and for 2 min post-injection by placing a tourniquet around the upper leg (just proximal to/or partially over the quadriceps muscle group). Subsequently 1.5 ml of a papaverine solution was injected (250 μg papaverine in 1.5 ml NSS) at a distal site in the great saphenous vein. Papaverine was pre-injected to stimulate vasodilation and increases vascular permeability (Budker et al. 1998, Lee et al. 1978). Two minutes after the papaverine injection, pDNA (pCI-Luc-K in normal saline solution) was injected into the great saphenous vein of the distal hind limb at a rate of 3 ml per ~20 seconds (10 ml/min; FIG. 1). The intravenous injections were performed in an anterograde direction (i.e., with the blood flow) via a needle catheter connected to a programmable Harvard PHD 2000

| | Quad | Biceps | Hamstring | Gastroc | Shin | Foot | total |
|---|---|---|---|---|---|---|---|
| Tissue Weight (g) | 1.57 | 1.28 | 1.5 | 1.1 | 0.55 | 0.06 | 6.06 |
| Luciferase RLUs | 7,016,230 | 69,733,530 | 8,775,140 | 14,942,710 | 3,289,150 | 4950 | 103,761,710 |
| Luciferase (ng) | 537 | 5335 | 671 | 1143 | 83.9 | 0.05 | 7770 |
| ng Luciferase/ g Muscle | 342 | 4168 | 448 | 1039 | 152 | 0.8 | 1282 |

Figure 10:
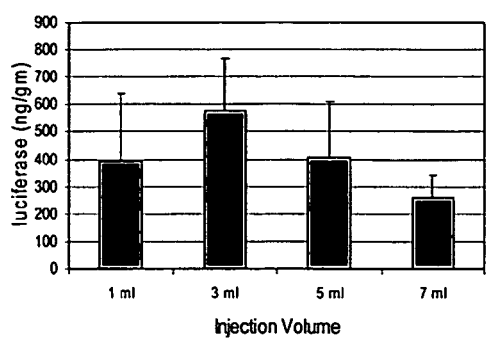
FIG. 10A-10B. Graph illustrating the effects of volume of injection (A) and rate of injection (B) on luciferase expression following intravenous delivery of pDNA (pCI-Luc-K) into the hind limbs of female Sprague-Dawley rats (120-150 g). For each data point, 2 to 7 limbs were injected and analyzed. T-bars indicate standard deviation.
Figure 10:
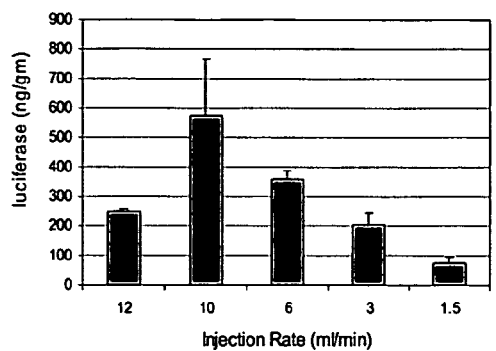

C. Injection into the great (medial) saphenous vein. An incision was made extending from the groin to the ankle. A segment of the distal medial saphenous vein was dissected free and a clamp was placed on the distal vein. In this experiment, the proximal femoral vein and artery and the epigastric artery and vein were dissected free and clamped as well as. A pretreatment of papaverine (2.0-2.5 ml) was injected antegrade by hand into the saphenous vein. After 5 minutes, a 27 gauge butterfly needle catheter was inserted into the saphenous vein and connected to a syringe pump. 5.0 ml of plasmid DNA (250 μg) was then injected at a flow rate of 10 ml/min. The lower limb muscles were swollen and some leakage occurred from the injection site as the injection progressed.

syringe pump (Harvard Instruments). Luciferase expression was determined as above. The venous procedure facilitated high level gene delivery to nearly all limb muscle groups distal to blood vessel occlusion (>500 ng luciferase per gram of muscle of lower limb) (FIG. 10). Highest delivery efficiencies were observed using an injection volume of 3 ml (when using 500 μg of pDNA) and an injection rate of between 6 and 12 ml per min. Expression was dose dependent and higher luciferase levels (~1000 ng/g muscle) were achieved by simply increasing the amount of pDNA injected.

Luciferase expression in individual muscle groups (ng Luciferase/g Muscle).

|  | Quad | Biceps | Hamstring | Gastroc | Shin | Foot | Total |
|---|---|---|---|---|---|---|---|
| | | | Experiment #1 | | | | |
| Rat #1 | 409 | 275 | 685 | 859 | 433 | 5.5 | 548 |
| Rat #2 | 197 | 213 | 729 | 1142 | 244 | 4.5 | 549 |
| Rat #3 | 85 | 312 | 360 | 311 | 76 | 0.3 | 257 |
| Mean ± St. Dev. | 230 ± 165 | 267 ± 50 | 592 ± 202 | 771 ± 422 | 251 ± 179 | 3.4 ± 2.7 | 452 ± 168 |
| | | | Experiment #2 | | | | |
| Rat #1 | 71 | 228 | 745 | 1163 | 307 | 5.6 | 559 |
| Rat #2 | 34 | 378 | 1259 | 1939 | 1226 | 7.8 | 907 |
| Rat #3 | 143 | 191 | 1634 | 468 | 187 | 6.3 | 580 |
| Rat #4 | 425 | 587 | 740 | 936 | 184 | 0.2 | 637 |
| Mean ± St. Dev. | 168 ± 177 | 346 ± 180 | 1095 ± 435 | 1127 ± 614 | 476 ± 503 | 5.0 ± 3.3 | 671 ± 161 |

Data represents results from 2 different experiments performed on different days (Expt. 1, n=3; Expt. 2, n=4).

Figure 11:
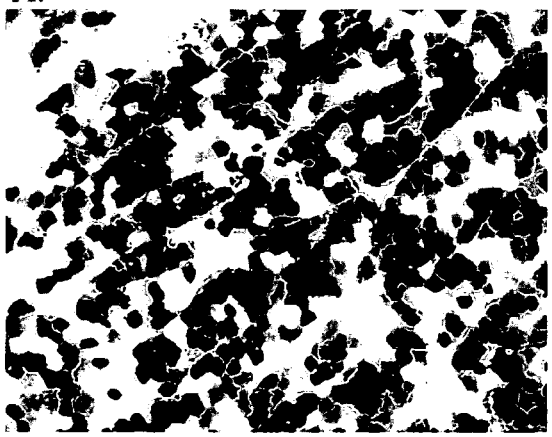
FIG. 11 Photomicrographs of rat limb gastrocnemius (A) and shin (B) muscles stained for β-galactosidase following repeat (triple) intravenous injections of 500 μg of pDNA (pCI-LacZ).
Figure 11:
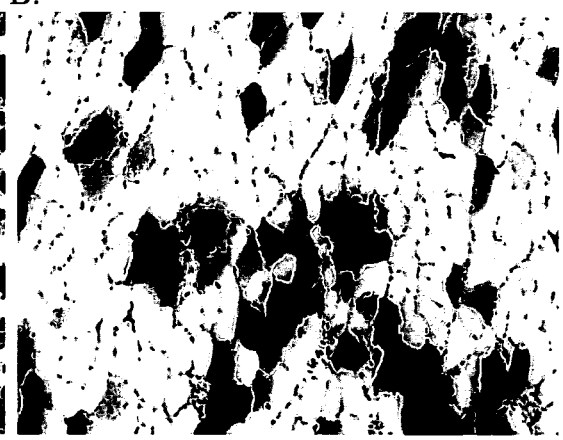

B. Multiple (repeat) injections: A Sprague-Dawley rat was injected intravenously as describe above except that animal were injected three-times with 500 μg of pCI-LacZ on days 0, 4, and 8 and muscles were harvested on day 10. Injections were performed, via catheterization, on days 0, 4, and 8 at different sites: lateral plantar vein, small saphenous, and great saphenous respectively. β-galactosidase staining was performed to analyze distribution of transfected cells. Additional injections resulted in significantly higher percentages of cells expressing the transgene (FIG. 11). In the gastrocnemius of the rat limb that was thrice injected, β-galactosidase expression was observed in about 60-80% of the cells in high-expressing areas (FIG. 11). β-galactosidase enzyme assays on the individual muscle groups correlated the histochemical analyses, 52,959,500 RLUs in the gastrocnemius muscle and 11,894,700 RLUs in the shin muscle.

C. Injection without vasodilator: Injections were performed as described above with the following differences: animal received papaverine injections at different times or did not receive papaverine injections. In rats receiving papaverine pre-injection, 1 or 5 min later pDNA was injected into the great saphenous vein of the distal hind limb at a rate of 3 ml per ~20 seconds (10 ml/min; FIG. 1). In rats not receiving papaverine injection, pDNA in 4.5 ml saline (same total volume injected) was injected in 30 sec. The results indicate that polynucleotides are effectively delivered to limb skeletal muscle cells, as evidenced by luciferase expression, both with and without pre-injection of a vasodilator.

Delivery of nucleic acid to limb muscle cells with and without vasodilator pre-injection.

D Intravenous delivery of polynucleotides to muscles of the foot: This experiment was performed as above 5 with the following differences: A tourniquet was placed just above the ankle and 100 μg luciferase encoding plasmid DNA in 1 ml saline was injected in a retrograde direction at a rate of 10 ml/min into the lateral plantar vein using a 30 gauge needle catheter. No pre-injection of papaverine was performed. In two animals, the average luciferase expression in muscles of the foot was 584±58.6 ng luciferase per gram of muscle tissue. Luciferase expression was minimal in the gastrocnemius muscles (muscle proximal to the tourniquet) of the same animals.

E. Effect of time of vessel occlusion following polynucleotide injection: These experiments were performed as above with the following differences: 250 μg of pMIR48 plasmid was injected and blood flow into and out of the injected leg was blocked for 0 min, 2 min, or 5 min following completion of the injection of the solution containing the polynucleotide into the vein. Blood flow was restored at the indicated time by release of the tourniquet. There was no papaverine pre-injection, and the DNA was in 4.5 ml saline solution injected in 30 sec. The results indicate that restricting blood flow for a long or shorter period following injection does not eliminate polynucleotide delivery to cells in the limb.

Delivery of polynucleotides to muscles throughout rat hind limb via intravenous injection; effect of maintenance of vessel occlusion after injection.

| | ng luciferase per gram muscle tissue | | | | | |
|---|---|---|---|---|---|---|
| pre-injection | quad | biceps | hamstring | gastroc | shin | total |
| 5 min | 99 ± 46 | 397 ± 188 | 248 ± 41 | 626 ± 363 | 122 ± 84 | 300 ± 87 |
| 1 min | 147 ± 107 | 309 ± 99 | 206 ± 36 | 398 ± 116 | 93 ± 61 | 242 ± 51 |
| none | 106 ± 37 | 328 ± 43 | 406 ± 91 | 874 ± 312 | 120 ± 17 | 387 ± 62 |

| | ng Luciferase per gm muscle tissue | | | | | |
|---|---|---|---|---|---|---|
| treatment | quad | biceps | hamstring | gastroc | shin | total |
| 5 min (n = 3) | 88 ± 42 | 342 ± 116 | 287 ± 82 | 665 ± 407 | 115 ± 44 | 339 ± 139 |
| 2 min (n = 2) | 81 ± 24 | 182 ± 26 | 407 ± 86 | 568 ± 60 | 27 ± 4 | 274 ± 29 |
| 0 min (n = 3) | 99 ± 26 | 184 ± 32 | 210 ± 15 | 399 ± 22 | 91 ± 23 | 210 ± 17 |

F. Effect of volume of injection solution and rate of injection on IV delivery of polynucleotides to limb skeletal muscle cells in rat and mouse. IV injections into rat were performed as above, except that the injection solution was injected at varying rates.

Delivery of polynucleotides to rat limb muscle cells using various injection rates.

| | study 1 | | | | study 2 | |
|---|---|---|---|---|---|---|
| | injection rate ml/min | | | | | |
| | 12 | 6 | 3 | 1.5 | 1 | 0.6 |
| ng luciferase per g tissue | 252 ± 6 | 358 ± 28 | 206 ± 41 | 76 ± 21 | 128 ± 32 | 97 ± 8.3 |

Example 20

Determination of Percentage of Transfected Myofibers

Intravenous injections of pCI-LacZ plasmid DNA were performed into the distal limbs of rats (great saphenous vein) as described above. For β-galactosidase staining, samples were taken from each muscle group, frozen in cold isopentane and stored at −80° C. 10 μm thick cryostat sections were cut from portions of the proximal, middle and distal locations of each muscle group. The sections were fixed and incubated in an X-gal staining solution (Mirus Corporation, Madison, Wis.) for one hour at 37° C. To maximize visualization of the blue cells (i.e., β-galactosidase positive), gastrocnemius sections (A) were not counterstained. All shin muscle sections were counter stained with hematoxylin (B). To minimize immune effects related to expression of the foreign protein (β-galactosidase) all rats were immunosuppressed. Animals received both FK-506 (2.5 mg/kg, PO) and dexamethasone (1 mg/kg, IM) one day before injection, one hour before injection and one day after injection. Animals then continued to receive FK506 (2.5 mg/kg, PO) every day throughout the study.

Figure 12:
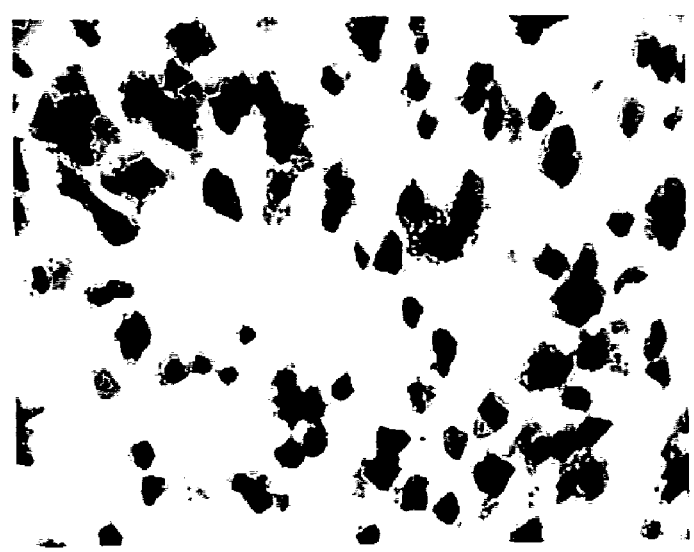
FIG. 12 Photomicrographs of rat limb gastrocnemius muscle stained for β-galactosidase following single intravenous injections of 500 μg of pDNA (pCI-LacZ).

After a single intravenous injection of 500 μg of pCI-LacZ (in 3 ml NSS over 20 s), β-galactosidase expression was detected in all muscle groups (range of 3-45% β-galactosidase positive cells) of the lower limb distal to the tourniquet (FIG. 12). One of the highest expressing muscle groups was the gastrocnemius in which approximately 30-45% of cells stained positive for the transgene in high expressing areas of the muscle (FIG. 12).

Example 21

Intravenous Delivery of a Gene Encoding a Secreted Protein

To determine if intravenous gene delivery to muscle could be used to deliver a secreted protein into the bloodstream, single and repeat intravenous injections of pCMV-hSEAP were performed using a secreted reporter gene expression construct. At day 8 post-injection, rats injected once (at day 0, as describe above) had mean serum hSEAP concentrations of 374 ng/ml (±264, n=3), while rats that received 2 injections (at days 0 and 5) had mean concentrtions of 631.6 ng/ml (±156, n=5).

Figure 13:
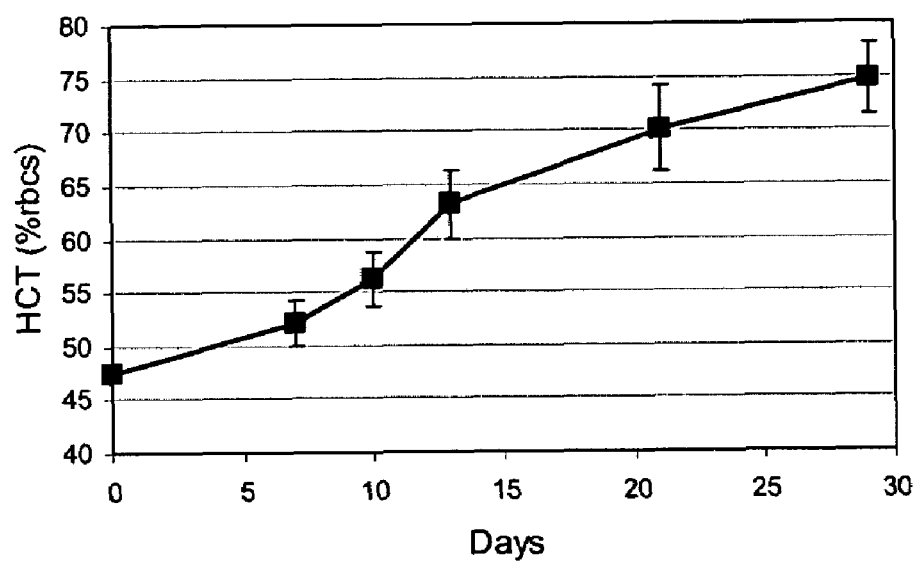
FIG. 13 Intravascular injection of therapeutic genes into mammalian limbs. Time course of erythropoietin expression following injection of 500 μg pDNA (in 3 ml NSS/20 s) encoding rat erythropoietin into great saphenous vein of distal limb of 120-150 g female Sprague-Dawley rats (n=3).

Rats injected with a polynucleotide (pMIR59, injections as described above) encoding the therapeutically relevant erythropoietin had their hematocrits increase continuously from a baseline of 47% to ~75% within the first 29 days (FIG. 13).

Example 22

Figure 14:
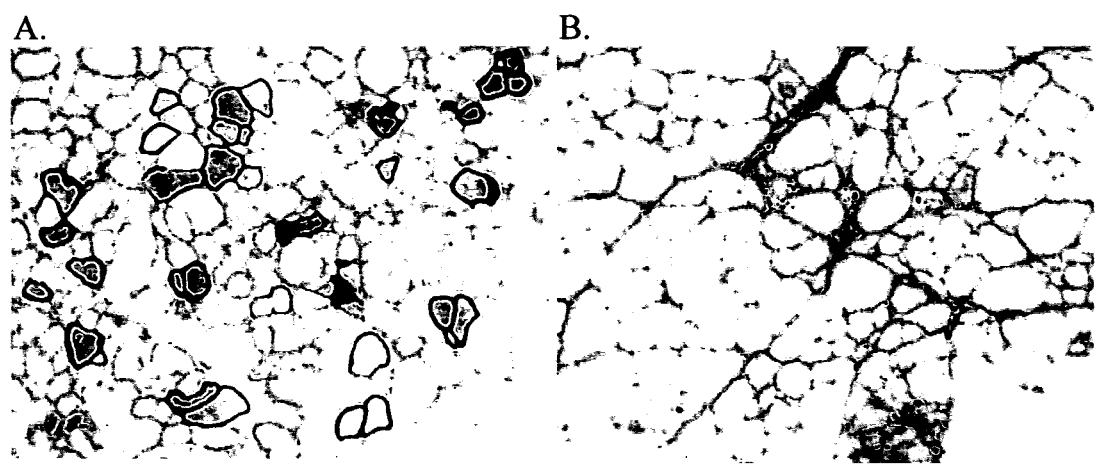
FIG. 14 Intravascular injection of therapeutic genes into mammalian limbs. Immunohistochemical staining for human dystrophin expression in mdx4cv mouse gastrocnemius muscle (left panel) one week after intravenous injection of 300 μg of a pDNA human dystrophin expression vector in 0.6 ml of NSS (7.5 s injection). Staining in mdx4cv mice injected with pCI-Luc negative control vector is shown in the right panel.

Intravenous Delivery of the Therapeutically Relevant Dystrophin Gene to Limb Muscle Cells in Mouse 300 μg of a pDNA human dystrophin expression vector (Acsadi et al. 1991) in 0.6 ml of NSS (7.5 s injection) was injected into a distal site in the great saphenous vein of the mdx4cv B6Ros.Cg-DM$^{mdx-4Cv}$ mouse (model for Duchenne muscular dystrophy, Jackson laboratory) hindlimb. Fluid flow into and out of the leg was occluded by means of a tourniquet. Blood flow was occluded prior to injection and for two minutes following the injection. Immunohistochemical staining for human dystrophin expression in mdx4cv mouse muscle (from gastrocnemius) was performed one week post-injection using a mouse, anti-dystrophin polyclonal primary antibody and a FITC-conjugated goat, anti-mouse IgG (FAB specific; Sigma) secondary antibody. Similar percentages of dystrophin-positive myofibers were detected using a monoclonal antibody specific for human dystrophin (NCL-DYS3, Novocastra Laboratories). Images were captured using a 10× objective (Zeiss Axioplan 2 fluorescent microscope). In four mdx4cv mice injected once intravenously with a plasmid expression vector encoding full-length, human dystrophin, 3-15% of myofibers of various hindlimb muscles exhibited sarcolemmal dystrophin expression (FIG. 14). Dystrophin-positive revertants in this particular mdx strain are below 0.5% (FIG. 14). The ability to perform the intravenous procedure in mouse models enhances its utility as a research tool.

Example 23

Effect of Injection Rate and Volume on IV Delivery of Polynucleotides to Mouse

IV injections into C57 mice were performed as in above, except that the injection solution volume and injection rate were varied.

Delivery of polynucleotides to mouse limb muscle cells using various injection volumes and rates.

| injection volume | enzyme activity | injection rate (ml/min) | | | | | |
|---|---|---|---|---|---|---|---|
| | | 2 | 4 | 8 | 12 | 15 | 18 |
| 0.2 ml | luciferase | | | | | 113 | |
| | CPK | | | | | 416 | |
| | | | | | | n = 2 | |
| 0.4 ml | luciferase | | | | | 253 | |
| | CPK | | | | | 403 | |
| | | | | | | n = 4 | |
| 0.6 ml | luciferase | 229 | 411 | 460 | 423 | 626 | 808 |
| | CPK | 194 | 356 | 163 | 1227 | 1018 | 320 |
| | | n = 3 | n = 3 | n = 3 | n = 3 | n = 4 | n = 3 |
| 0.8 ml | luciferase | | 232 | 385 | 462 | 375 | 203 |
| | CPK | | 878 | 298 | 1600 | 1710 | 754 |
| | | | n = 2 | n = 2 | n = 1 | n = 6 | n = 3 |
| 1.0 ml | luciferase | 299 | 264 | 518 | 497 | 606 | 612 |
| | CPK | 286 | 329 | 216 | 330 | 277 | 511 |
| | | n = 2 | n = 4 | n = 6 | n = 10 | n = 9 | n = 5 |
| 1.25 ml | luciferase | 109 | 426 | 882 | | 310 | |
| | CPK | | | | | 638 | |
| | | n = 1 | n = 2 | n = 2 | | n = 4 | |
| 1.5 ml | luciferase | 154 | 549 | 1050 | 482 | 706 | 561 |
| | CPK | 319 | 522 | 573 | 279 | 515 | 237 |
| | | n = 1 | n = 2 | n = 2 | n = 2 | n = 2 | n = 1 | luciferase = ng/g tissue
CPK = U/L

Example 24

Intravenous Delivery of Polynucleotides to Limb Muscle Cells in Dog 9.5 kg beagles were induced with acepromazine (0.1 mg/kg, SQ) and morphine (1.5 mg/kg, IM) followed 10-20 minutes later by thiopental (10-15 mg/kg, IV). Animals were then intubated, connected to an anesthesia machine and maintained with 1 to 2% isoflurane. A front limb to be injected was shaved and a modified pediatric blood pressure cuff was attached just above the elbow. A 20 gauge intravenous catheter (length=1.8 inches) was inserted into the distal cephalic vein and secured with tape. The catheter was then connected to a three-way stopcock and flushed with about 2 ml saline to remove any blood in the catheter. After inflating the blood pressure cuff to a pressure greater than 300 mmHg to impede fluid flow to and from the limb, 25 ml NSS containing 4.2 mg papaverine (Sigma) and 150 units of heparin was injected by hand over 10 seconds. For the pDNA injection, the three-way stopcock was connected to two PHD 2000 syringe pumps each loaded with a single syringe. Five minutes after the papaverine injection, 20 mg of pCI-Luc-K in 36-40 ml NSS were injected at a rate of 2 ml per second. Two minutes after the polynucleotide injection, the blood pressure cuff was released and the catheter was removed. Animals were given analgesics (buprenorphine, 0.01 to 0.02 mg/kg, IM) once at the time of the injection and again after the procedure. The left front limb was injected on day 0 and the right front limb was injected on day 3. After recovering from anesthesia, animals were able to move around freely using the injected limb. 24 hours after injection there was no sign of swelling in the injected limb.

Luciferase expression in dog (beagle) forelimb muscle cells following in vivo IV delivery of plasmid encoding the luciferase gene.

| Limb | Injection Site | Volume (ml) | pDNA (mgs) | Rate (ml/sec) | Total Luciferase per Leg (ng/g) |
|---|---|---|---|---|---|
| front (right) | cephalic vein | 40 | 20 | 2.0 | 93 (day 4) |
| front (left) | cephalic vein | 36 | 20 | 2.0 | 419 (day 7) |

Luciferase activity in dog forelimb muscle cells following in vivo IV delivery of plasmid encoding the luciferase gene.

| Muscle group | Muscle name | ng Luciferase/ g muscle | |
|---|---|---|---|
| | | 4 day | 7 day |
| Dorsolateral antebrachial muscles | Extensor carpi radialis | 135.6 | 2297.8 |
| | Extensor digitorum communis | 552.1 | 421.1 |
| | Extensor digitorum lateralis | 77.9 | 488.7 |
| | Extensor carpi ulnaris | 22.9 | 22.4 |
| | Extensor pollicis longus et indicis proprius | 222.8 | 60.8 |
| | Supinator | 262.6 | 182.6 |
| Caudal antebrachial muscles | Flexor carpi radialis | 14.3 | 294.7 |
| | Flexor carpi ulnaris | 3.5 | 14.4 |
| | Flexor digitorum superficialis | 49.1 | 47.6 |
| | Flexor digitorum profundus | 55.5 | 160.8 |
| | Pronator teres | 35.5 | 333.7 |
| | Pronator quadratus | 260.7 | 230.2 |
| Muscles of forepaw | Muscles of forepaw | 89.2 | 123.6 |
| | Weighted average: | 92.6 | 419.1 |

A weighted average was calculated by dividing the total luciferase expressed (in nanograms) by the total weight of the limb muscles analyzed (in grams).

Example 25

Intravenous Delivery of Polynucleotides into Primate (Rhesus Monkey)

Three adult rhesus primates were used in this study. Primate #1 was a 8.8 kg male, primate #2 was a 6.0 kg female and primate #3 was a 4.2 kg male. Animals were induced with ketamine (15 mg/kg, IM), intubated and anesthesia maintained with 1-2% isoflurane. The limb to be injected was shaved and a modified pediatric blood pressure cuff (sphygmomanometer) was attached just proximal the elbow (or knee). A 22 gauge intravenous catheter (length=1.0 inches) was inserted into the selected vein (great saphenous, small saphenous, cephalic or median vein) and secured with tape. The catheter was then connected to a three-way stopcock and flushed with saline. After inflating the blood pressure cuff to a pressure greater than 300 mmHg, to block inflow and outflow of blood in the distal limb (FIG. 1C), a 20-30 ml saline solution containing 5 mg of papaverine and 150 Units of heparin was injected by hand over 10 seconds. For the pDNA injection, the three-way stopcock was connected to two syringe pumps each loaded with a single syringe. 5 min after the papaverine injection, pDNA (15.5-25.7 mg in 40-100 ml NSS) was injected at a rate of 1.7 or 2.0 ml per second. Two minutes after the pDNA injection, the blood pressure cuff was released and the catheter was removed. Animals were given analgesics (buprenorphine, 0.01 mg/kg, IM) once at the time of the injection and again after the procedure.

Primate #1 had the left forearm (16.5 mg pCI-Luc) and right hind limb (21.3 mg pCI-Luc) injected on day 0 and the right forearm (15.5 mg pCI-Luc) and left hind limb (25.7 mg pCI-Luc) injected on day 3. Primate #2 had the left forearm (20 mg pCI-Luc-K) and the right hind limb injected (20 mg pCI-LacZ) on day 0 and the right forearm (20 mg pCI-Luc-K) and the left hind limb injected (20 mg pCI-LacZ) on day 3. Primate #3 had the left forearm (20 mg pCI-Luc-K) and right hind limb (40 mg pCI-LacZ) injected on day 0 and the right forearm (plasmids plus siRNA) and left hind limb (plasmids plus siRNA) injected on day 3. After recovering from anesthesia, the animals were able to move around freely using the injected limbs. Twenty four hours after injection there was only minor swelling and small areas of bruising in the injected limb.

Animals were euthanized on the indicated days and luciferase assays, muscle sectioning, hemotoxylin counterstaining and β-galactosidase staining were performed as described for rat studies. Photomicrographs were captured using a 10× or 20× objective (Zeiss Axioplan 2 microscope). Percent β-galactosidase positive cells were quantitated by dividing the total number of blue stained cells by the total number of myofibers on a given section and multiplying by 100.

Luciferase expression in rhesus monkey limb muscle cells following in vivo IV delivery of plasmid encoding the luciferase gene.

| Animal | Limb | Injection Site | Volume (ml) | pDNA (mgs) | Rate (ml/sec) | Total Luciferase per leg (ng/g) |
|---|---|---|---|---|---|---|
| 1 | arm | cephalic vein | 100 | 16.5 | 1.7 | 513 (day 7) |
| 1 | leg | small saphenous vein | 100 | 21.3 | 1.7 | 543 (day 7) |
| 1 | arm | cephalic vein | 70 | 19.8 | 2.0 | 215 (day 4) |
| 1 | leg | great saphenous vein | 90 | 19.8 | 2.0 | 464 (day 4) |
| 2 | arm | cephalic vein | 40 | 20 | 2.0 | 386 (day 7) |
| 2 | arm | median vein | 40 | 20 | 2.0 | 98.2 (day 4) |

Luciferase expression in rhesus monkey arm muscle cells following in vivo IV delivery of plasmid encoding the luciferase gene

| | | ng Luciferase/g muscle | | | |
|---|---|---|---|---|---|
| | | Primate #1 | | Primate #2 | |
| Muscle group | Muscle name | Day 4 | Day 7 | Day 4 | Day 7 |
| Anterior group | | | | | |
| Superficial group | Palmaris longus | 52.0 | 317.7 | 6.2 | 74.4 |
| | Pronator teres | 27.8 | 85.3 | 268.9 | 266.6 |
| | Flexor carpi radialis | 330.2 | 497.4 | 846.3 | 1322.1 |
| | Flexor carpi ulnaris | 32.0 | 26.8 | 20.9 | 566.0 |
| | Flexor digitorum spf. | 54.2 | 102.3 | 3.3 | 54.2 |
| Deep group | Flexor digitorum prof. | 108.5 | 177.4 | 11.6 | 156.7 |
| | Pronator quadratus | 525.3 | 250.1 | 54.3 | 188.4 |
| Posterior group | | | | | |
| Superficial group | Brachioradialis | 242.5 | 1507.8 | 165.6 | 1439.8 |
| | Extensor carpi radialis longus | 144.4 | 1251.6 | 2.3 | 25.9 |
| | Extensor carpi radialis brevis | 99.1 | 776.5 | 32.8 | 78.9 |
| | Extensor digitorum | 1316.8 | 1229.6 | 28.8 | 343.8 |
| | Anconeus | 286.4 | 156.9 | 29.3 | 336.8 |
| | Extensor carpi ulnaris | 258.2 | 748.9 | 5.4 | 29.4 |
| | Extensor pollicis longus | 251.5 | 90.9 | 5.6 | 106.7 |
| Deep group | Supinator | 553.3 | 584.4 | 80.6 | 640.9 |
| | Abductor pollicis longus | 327.5 | 261.4 | 26.5 | 354.4 |
| | Extensor digiti secund et teriti | 385.5 | 379.2 | na* | na |
| | Extensor digiti quart et minimi | 336.8 | 314.0 | 11.1 | 111.7 |
| Muscles of the hand | Thumb muscles | 455.4 | 1047.5 | 30.6 | 180.2 |
| | Interosseus | 598.0 | 1365.8 | 202.5 | 837.3 |
| | Others | 525.6 | 55.7 | 11.6 | 61.4 |
| Weighted average: | | 215.0 | 542.1 | 98.2 | 385.9 | na = not asssayed

Luciferase expression (ng/g muscle) in Rhesus Macaque Leg Muscles

|  | ng Luciferase/g muscle | |
| --- | --- | --- |
| Muscle name | Day 4 (ng/g) | Day 7 (ng/g) |
| Gastrocnemius | 455.2 | 261.2 |
| Soleus | 1464.3 | 1038.9 |
| Popliteus | 2442.4 | 452.5 |
| Flexor digitorum longus | 75.4 | 985.9 |
| Flexor hallucis longus | 117.2 | 555.8 |
| Tibialis posterior | 400.5 | 788.5 |
| Tibialis anterior | 266.1 | 222.4 |
| Extensor hallucis longus | 197.9 | 377.0 |
| Extensor digitorum longus | 969.0 | 1994.7 |
| Abductor hallucis longus | 61.3 | 85.6 |
| Peronaus longus | 207.6 | 824.4 |
| Peronaus brevis | 59.2 | 733.7 |
| Extensor digitorum brevis | 1.6 | 6.4 |
| Extensor hallucis brevis | 10.3 | 123.7 |
| Other foot muscles | 4.7 | 123.0 |
| Weighted average: | 464.5 | 513.4 |

Figure 15:
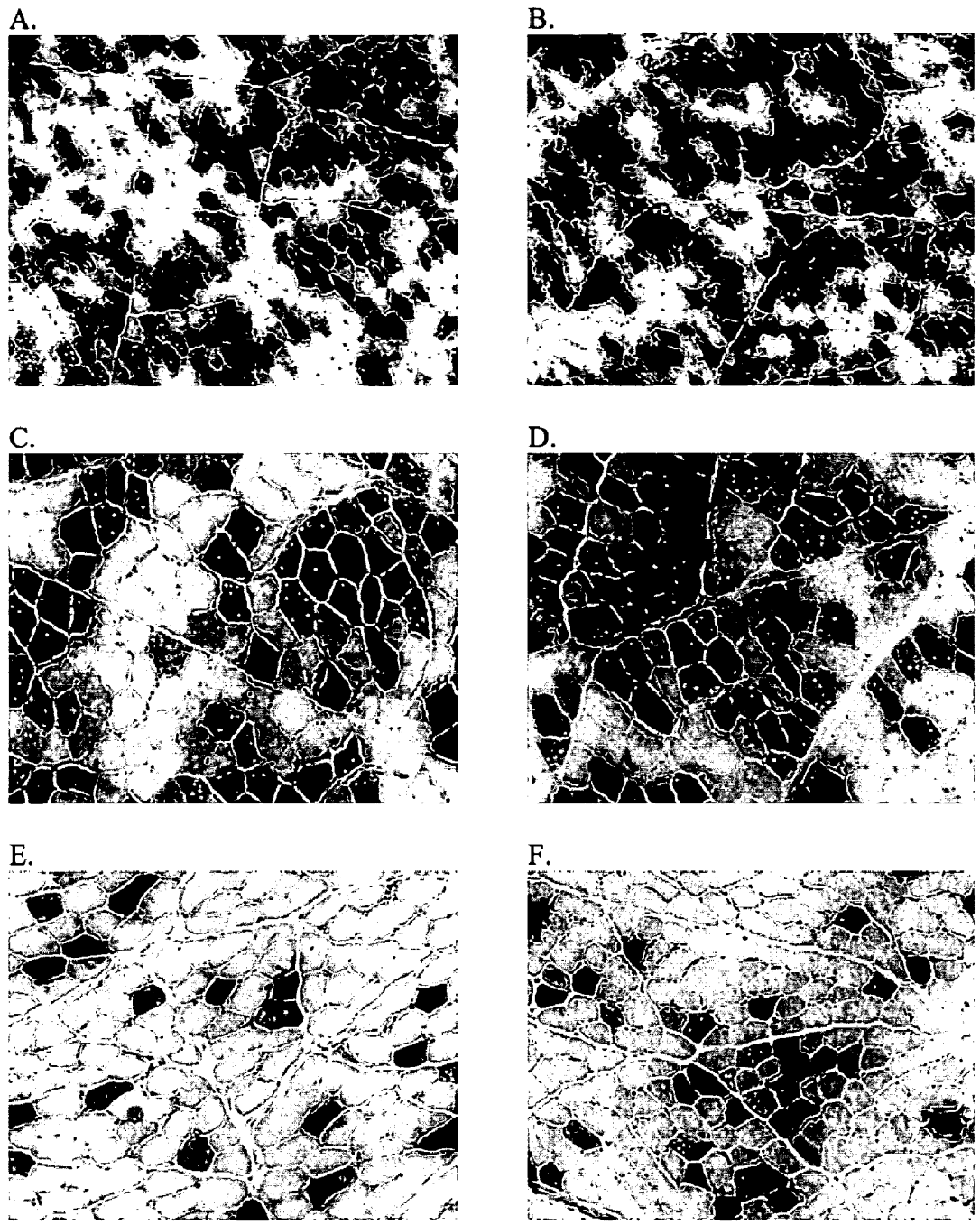

Intravenous injections with pCI-LacZ and subsequent β-galactosidase histochemical analyses indicate that myofibers were transfected in primates as in rats. In the hind limb of primate #2 injected with pDNA encoding β-galactosidase, expression was observed in all muscle groups of the lower limbs. The percentage of transfected myofibers in high expressing areas of three targeted muscle groups (gastrocnemius, soleus, extensor hallucis brevis) ranged from 11% to 49% (FIG. 15). For two of the targeted distal limb muscle groups (soleus muscle, small muscles of the foot) a more quantitative analysis was performed by counting β-galactosidase positive cells from multiple sections chosen randomly throughout the muscle group. Using this analysis technique, the soleus muscle showed an overall transfection efficiency of 25.4% (2453 lacZ positive cells/9650 total cells counted) while the small muscles of the foot displayed an overall transfection efficiency of 7.3% (205 lacZ positive cells/2805 total cells counted).

Example 26

Intravenous Delivery of siRNAs into Rat and Primate Limb Muscle Cells

RNA interference is a recently recognized phenomenon in which target gene expression (in mammalian cells) can be selectively inhibited following the introduction of double stranded RNA into a cell (Elbashir et al. 2001). To delivery siRNA to extravascular limb cells to achieve RNA interference in myofibers in vivo, siRNAs (targeted against firefly luciferase) were co-injected with pDNA encoding firefly luciferase (pCI-Luc-K) into the great saphenous vein of C57Bl/6 mice, Sprague-Dawley rats and a rhesus macaque. At 2 days post-injection, greater than 95% inhibition of the targeted gene was achieved in the limbs that received the siRNA encoding the firefly luciferase in all three species (FIG. 16).

For delivery of siRNA to rat limb muscle cells, 150 g Sprague Dawley rats were co-injected into the great saphenous vein with 250 μg of a pDNA encoding firefly luciferase (pSP-luc$^+$, Promega) and 25 μg of a pDNA (pRL-SV40, Promega) encoding *Renilla reniformis* luciferase. Injections were performed using 3 mls injection volume as described above. One group of animals (n=5) received plasmids alone, one group (n=5) received plasmids plus 12.5 μg of a siRNA targeted against firefly luciferase (siRNA-luc$^+$) and a control group (n=5) received plasmids plus 12.5 μg of a siRNA targeted against enhanced green fluorescent protein (siRNA-EGFP, Clontech). Muscle was harvested 72 hours after injection.

Expression levels were measured by preparing homogenates and measuring activity of the firefly luciferase and the *renilla* luciferase using the dual luciferase assay kit (Promega). The mean expression levels (from all harvested muscle groups) in animals receiving the siRNA targeted against firefly luciferase was normalized to those animals receiving the control siRNA (EGFP). Animal receiving siRNA against firefly luciferase showed ~60 fold reduction in firefly luciferase expression relative to *Renilla* luciferase expression.

|  | Muscle Group | | | | | |
| --- | --- | --- | --- | --- | --- | --- |
|  | quad | biceps | hamstring | gastroc | shin | total |
| no siRNA | | | | | | |
| average firefly luciferase expression | 2,331,015 | 2,197,626 | 5,701,719 | 6,368,653 | 648,859 | 17,247,871 |
| average *Renilla* luciferase expression | 102,322 | 98,349 | 242,450 | 319,224 | 31,129 | 793,474 |
| average ratio (firefly/*Renilla*) | 23.4 ± 4.5 | 22.3 ± 4.0 | 23.8 ± 3.4 | 22.2 ± 4.7 | 21.3 ± 1.7 | 22.8 ± 3.1 |
| control siRNA | | | | | | |
| average firefly luciferase expression | 692,220 | 2,317,722 | 4,767,100 | 5,296,748 | 514,189 | 12,425,792 |
| average *Renilla* luciferase expression | 25,566 | 105,572 | 188,049 | 252,630 | 24,196 | 540,647 |
| average ratio (firefly/*Renilla*) | 25.6 ± 6.5 | 24.1 ± 3.7 | 26.3 ± 5.2 | 22.2 ± 3.5 | 21.3 ± 0.9 | 24.3 ± 3.9 |

-continued

|  | Muscle Group | | | | | |
| --- | --- | --- | --- | --- | --- | --- |
|  | quad | biceps | hamstring | gastroc | shin | total |
| siRNA | | | | | | |
| average firefly luciferase expression | 44,754 | 103,421 | 105,719 | 223,126 | 54,779 | 531,799 |
| average Renilla luciferase expression | 115,517 | 292,509 | 300,648 | 521,484 | 104,106 | 1,334,265 |
| average ratio (firefly/Renilla) | 0.46 ± 0.20 | 0.37 ± 0.04 | 0.35 ± 0.05 | 0.44 ± 0.04 | 0.49 ± 0.09 | 0.40 ± 0.03 |

For delivery of siRNA to primate limb muscle cells, injection parameters were used as described above for plasmid delivery studies. One front limb of a rhesus macaque was injected via the cephalic vein with 40 ml of saline containing 10 mg of a pDNA encoding firefly luciferase (pCI-Luc-K), 2.2 mg of a pCMV-*Renilla* encoding *Renilla reniformis* (sea pansy) luciferase and 750 µg of a siRNA targeted against firefly luciferase (siRNA-luc$^+$). The opposite lower hind limb was injected on the same day via the great saphenous vein with 50 ml of saline containing the same plasmids plus 750 µg of a siRNA targeted against enhanced green fluorescent protein (siRNA-EGFP). 96 hours after injection, animals were euthanized and muscles were harvested. Expression levels were measured with the same technique described in the rat studies. Data was normalized to values obtained for the control siRNA (EGFP). Co-delivery of a plasmid containing an expressible reporter gene was used as a convenient method to quantitatively assay delivery of the siRNA. The invention does not require co-delivery of a plasmid for delivery of siRNA and absence of plasmid DNA in the injection solution will not effect siRNA delivery. For all muscle groups of the forearm (palmaris longus, pronator teres, flexor carpi radialis, flexor carpi ulnaris, flexor digitorum superficial is, flexor digitorum profundus, pronator quadratus, brachioradialis, extensor carpi radialis longus, extensor carpi radialis brevis, extensor digitorum, anconeus, extensor carpi ulnaris, supinator, abductor pollicis longus, ext. digiti secund et teriti, extensor digiti quart et minimi, muscles of the thumb, interosseus, other, muscles of the hand), the ratio of firefly luciferase expression to *Renilla* luciferase expression was 0.019±0.015. For all muscle groups of the lower hind limb (gastrocnemius medial, gastrocnemius lateral, soleus, popliteus, flexor digitorum longus, flexor hallucis longus, tibialis posterior, tibialis anterior, extensor hallucis longus, extensor digitorum longus, abductor hallucis longus, peronaus longus, peronaus brevis, extensor digitorum brevis, extensor hallucis brevis, other muscles of the foot), the ratio of firefly luciferase expression to *Renilla* luciferase expression was 0.448±0.155. Muscles receiving the firefly specific siRNA showed 23.6 fold lower expression of firefly luciferase relative to *Renilla* luciferase.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. An in vivo process for delivering a nucleic acid to an extravascular cell in a limb of a mammal, comprising:
    a) forming a complex containing the nucleic acid in a pharmaceutically acceptable solution;
    b) inserting an injection devise into a vessel in the limb;
    c) applying a device to occlude blood flow externally around the limb;
    d) occluding blood flow to an from the limb; and,
    e) injecting the solution through the injector into the vessel thereby increasing permeability of the blood vessel, passing the nucleic acid though the blood vessel and delivering the nucleic acid to the extravascular cell.

2. The process of claim 1 wherein increasing the permeability of the vessel consists of increasing pressure against vessel walls.

3. The process of claim 2 wherein increasing the pressure consists of increasing a volume of fluid within the vessel.

4. The process of claim 1 wherein said device for impeding blood flow is selected from the group consisting of: tourniquet, double tourniquet, double cuff tourniquet, cuff, sphygmomanometer, oscillotonormeter, oscillometer, and haemotonormeter.

5. The process of claim 1 wherein the complex consists of a virus.

6. The process of claim 1 wherein the complex consists of a non-viral complex.

7. The process of claim 1 wherein the nucleic acid consists an oligonucleotide.

8. The process of claim 1 wherein the nucleic acid consists of double stranded nucleic acid.

9. The process of claim 1 wherein the nucleic acid consists of single stranded nucleic acid.

10. The process of claim 1 wherein the nucleic acid is selected from the list consisting of RNA, double strand RNA, siRNA, microRNA, and antisense nucleic acid.

11. The process of claim 1 wherein the extravascular cell consists of a muscle cell.

12. The process of claim 11 wherein the muscle cell consists of an arm muscle cell.

13. The process of claim 12 wherein the arm muscle cell is selected from the group consisting of palmaris longus muscle cell, pronator teres muscle cell, flexor carpi radialis muscle cell, flexor carpi ulnaris muscle cell, and flexor digitorum superficialis muscle cell.

14. The process of claim 12 wherein the arm muscle cell is selected from the group consisting of flexor digitorum profundus muscle cell, and pronator quadratus muscle cell.

15. The process of claim 12 wherein the arm muscle cell is selected from the group consisting of brachioradialis muscle cell, extensor carpi radialis longus muscle cell, extensor carpi radialis brevis muscle cell, extensor digitorum muscle cell, anconeus muscle cell, extensor carpi ulnaris muscle cell, and extensor pollicis longus muscle cell.

16. The process of claim 12 wherein the arm muscle cell is selected from the group consisting of supinator muscle cell, abductor pollicis longus muscle cell, extensor digiti secund et teriti muscle cell, and extensor digiti quart et minimi muscle cell.

17. The process of claim 11 wherein the muscle cell consists of an hand muscle cell.

18. The process of claim 17 wherein the hand muscle cell consists of a thumb muscle cell.

19. The process of claim 17 wherein the hand skeletal muscle cell is consists of an interosseus muscle cell.

20. The process of claim 11 wherein the muscle cell consists of a leg muscle cell.

21. The process of claim 20 wherein the leg skeletal muscle cell is selected from the group consisting of gastrocnemius muscle cell and soleus muscle cell.

22. The process of claim 20 wherein the leg skeletal muscle cell is selected from the group consisting of popliteus muscle cell, flexor digitorum longus muscle cell, flexor hallucis longus muscle cell, and tibialis posterior muscle cell.

23. The process of claim 20 wherein the leg skeletal muscle cell is selected from the group consisting of tibialis anterior muscle cell, extensor hallucis longus muscle cell, extensor digitorum longus muscle cell, and abductor hallucis longus muscle cell.

24. The process of claim 20 wherein the leg skeletal muscle cell is selected from the group consisting of peronaus longus muscle cell and peronaus brevis muscle cell.

25. The process of claim 11 wherein the muscle cell consists of a foot muscle cell.

26. The process of claim 25 wherein the foot skeletal muscle cell is selected from the group consisting of extensor digitorum brevis muscle cell and extensor hallucis brevis muscle cell.

27. The process of claim 1 further comprising administering immunosuppressive drugs to the mammal.

28. The process of claim 6 wherein non-viral complex comprises the nucleic acid and a cationic polymer.

29. The process of claim 28 wherein the cationic polymer consists of a polyamine.

30. The process of claim 29 wherein the polyamine is selected from the group consisting of histone, polvethyleneimine, poly-L-lysine, poly-histidine, and protamines.

31. The process of claim 6 wherein non-viral complex comprises the nucleic acid and a cationic lipid.

32. The process of claim 31 wherein non-viral complex consists of a lipopolyplex.

33. The process of claim 6 wherein the non-viral complex comprises the nucleic acid, a polycation and a polyanion.

34. The process of claim 33 wherein the net charge of the complex is negative.

35. The process of claim 6 wherein the non-viral complex comprises the nucleic acid, a cationic lipid and a polyanion.

36. The process of claim 35 wherein the net charge of the non-viral complex is negative.

* * * * *